(12) United States Patent
Matsuda et al.

(10) Patent No.: US 7,790,000 B2
(45) Date of Patent: Sep. 7, 2010

(54) VOLATILIZER

(75) Inventors: Eiko Matsuda, Hyogo (JP); Yasuko Umetani, Hyogo (JP); Ryuji Okano, Hyogo (JP); Nobuya Kubo, Hyogo (JP); Shusaku Tsutsumi, Hyogo (JP); Shoichi Kohmoto, Okayama (JP)

(73) Assignee: Earth Chemical Co., Ltd., Tokyo (JP)

( * ) Notice: Subject to any disclaimer, the term of this patent is extended or adjusted under 35 U.S.C. 154(b) by 1014 days.

(21) Appl. No.: 10/515,819

(22) PCT Filed: Dec. 27, 2002

(86) PCT No.: PCT/JP02/13842

§ 371 (c)(1),
(2), (4) Date: Feb. 9, 2006

(87) PCT Pub. No.: WO03/099343

PCT Pub. Date: Dec. 4, 2003

(65) Prior Publication Data

US 2006/0231213 A1   Oct. 19, 2006

(30) Foreign Application Priority Data

May 27, 2002 (JP) .............................. 2002-152618
Dec. 6, 2002 (JP) .............................. 2002-355194

(51) Int. Cl.
*B01D 3/00* (2006.01)
*B01D 15/00* (2006.01)
*A61L 9/04* (2006.01)

(52) U.S. Cl. .............. 202/183; 159/27.3; 159/DIG. 27; 159/DIG. 28; 202/184; 203/41; 203/95; 210/263; 210/664; 239/37; 239/44; 239/47

(58) Field of Classification Search ................ 159/27.3, 159/44, 906, DIG. 27, DIG. 28; 202/183, 202/184; 203/1, 41, 95; 210/263, 664; 239/37, 239/44, 47
See application file for complete search history.

(56) References Cited

U.S. PATENT DOCUMENTS 3,343,916 A * 9/1967 Cahn et al. .................. 423/359
3,587,968 A   6/1971 Hennart et al.
4,227,891 A * 10/1980 Maguire et al. ............... 95/208

(Continued)

FOREIGN PATENT DOCUMENTS

EP   1031446 A1   8/2000

(Continued)

OTHER PUBLICATIONS

Korean Office Action dated Jan. 12, 2009.

(Continued)

*Primary Examiner*—Virginia Manoharan
(74) *Attorney, Agent, or Firm*—Sughrue Mion, PLLC

(57) ABSTRACT

The present invention relates to an evaporation apparatus capable of supplying active ingredients sufficiently and stably. One embodiment of the invention includes a retention vessel keeping a liquid formulation which contains active ingredients, a liquid absorbing mechanism which absorbs the liquid formulation from said retention vessel, an evaporation mechanism which evaporates active ingredients of said liquid formulation absorbed into said liquid absorbing mechanism and adjusting means which adjusts the evaporation of active ingredients.

17 Claims, 20 Drawing Sheets

U.S. PATENT DOCUMENTS

| | | | |
|---|---|---|---|
| 4,323,193 | A | 4/1982 | Compton et al. |
| 4,475,988 | A * | 10/1984 | Tsumura et al. ............. 202/174 |
| 4,494,967 | A * | 1/1985 | Barth .......................... 95/193 |
| 4,840,773 | A | 6/1989 | Wade |
| 5,437,410 | A | 8/1995 | Babasade |
| 5,894,052 | A | 4/1999 | Sawyer |
| 5,901,710 | A * | 5/1999 | Barber ....................... 131/274 |
| 6,258,857 | B1 * | 7/2001 | Iijima et al. .................... 516/1 |
| 2006/0220267 | A1 * | 10/2006 | Kabasawa et al. ........... 261/142 |

FOREIGN PATENT DOCUMENTS

| | | |
|---|---|---|
| GB | 435246 | 4/1935 |
| GB | 2 180 450 A | 4/1987 |
| JP | 58-13248 U | 1/1983 |
| JP | 58-139142 U | 9/1983 |
| JP | 59-25755 A | 2/1984 |
| JP | 59-44443 U | 3/1984 |
| JP | 63-93935 U | 6/1988 |
| JP | 63-94174 U | 6/1988 |
| JP | 4-65550 U | 6/1992 |
| JP | 05-038585 A | 2/1993 |
| JP | 5-81080 U | 11/1993 |
| JP | 5-329221 A | 12/1993 |
| JP | 05-329221 A | 12/1993 |
| JP | 3024418 U | 2/1996 |
| JP | 8-58299 A | 3/1996 |
| JP | 8-107928 A | 4/1996 |
| JP | 8-282200 A | 10/1996 |
| JP | 9-276385 A | 10/1997 |
| JP | 09-276385 A | 10/1997 |
| JP | 11-262518 A | 9/1999 |
| JP | 2000-202014 A | 7/2000 |
| JP | 2000-245818 A | 9/2000 |
| WO | 01/91832 A1 | 12/2001 |

OTHER PUBLICATIONS

Japanese Office Action issued Sep. 10, 2008.
Japanese Office Action dated Nov. 11, 2008.
Japanese Office Action dated Feb. 10, 2009.

* cited by examiner

VOLATILIZER

TECHNICAL FIELD

The present invention relates to an evaporation apparatus which evaporates active ingredients.

BACKGROUND ART

Conventionally-known evaporation apparatuses are those in which a liquid formulation which contains active ingredients is absorbed into an evaporation body from which the active ingredients are evaporated.

However, such evaporation apparatuses are disadvantageous in that a liquid formulation absorbed into an evaporation body is evaporated before use or evaporation of active ingredients are not well adjusted during use of these apparatuses, thus making it difficult to keep the efficacy of active ingredients for a long period and leaving room for improvements.

An object of the invention is to provide an evaporation apparatus which is able to evaporate active ingredients sufficiently and stably.

DISCLOSURE OF THE INVENTION

The above object of the invention can be fulfilled by the following configurations.

(1) An evaporation apparatus comprising a retention vessel keeping a liquid formulation which contains active ingredients, a liquid absorbing mechanism which absorbs the liquid formulation from said retention vessel, an evaporation mechanism which evaporates active ingredients of said liquid formulation absorbed into said liquid absorbing mechanism and adjusting means which adjusts evaporation of active ingredients.

(2) The evaporation apparatus described in the above (1) comprising a liquid absorbing member at least partially exposed out of said retention vessel, a cylindrical inner member fixed so as to cover the exposed part of said liquid absorbing member, a cylindrical outer member fixed so as to cover said inner member and a rotating part attached to said inner member or said outer member, wherein an inner opening is provided on said inner member and an outer opening is provided on said outer member, and rotation of said rotating part allows said inner opening and said opening to communicate, by which said liquid absorbing member is exposed to evaporate active ingredients.

(3) The evaporation apparatus described in the above (2) comprising a clip connection and a clip having plural tightening parts, the one end of which is held with said clip connection, wherein other ends of said tightening parts are tightened to each other to provide an irregular surface on the contacting part.

(4) The evaporation apparatus described in the above (3) wherein said clip is fixed in an attachable and detachable manner on an outer vessel assembled to said retention vessel.

(5) The evaporation apparatus described in the above (1) having an evaporation carrier to which said liquid formulation is supplied through said liquid absorbing mechanism, wherein said evaporation carrier is provided with a body holding said liquid formulation and an erection part erected from said body.

(6) The evaporation apparatus described in the above (5) wherein a liquid absorbing member is kept exposed in or out of said retention vessel and said liquid formulation contained in said retention vessel is supplied via said liquid absorbing member into said evaporation carrier.

(7) The evaporation apparatus described in the above (5) comprising said retention vessel having a liquid absorbing member at a lower part which is at least partially exposed out of said retention vessel and an evaporation carrier to which said liquid formulation is supplied via said liquid absorbing member, wherein said evaporation carrier is made with porous materials and a liquid absorption quantity in about 50 minutes by said evaporation carrier with an area of 32 $mm^2$ and a thickness of 5 mm exceeds 7.5 g.

(8) The evaporation apparatus described in the above (5) comprising said retention vessel having a liquid absorbing member at a lower part which is at least partially exposed out of said retention vessel and an evaporation carrier to which said liquid formulation is supplied via said liquid absorbing member, wherein said liquid absorbing member contacts with said evaporation carrier on the surface.

(9) The evaporation apparatus described in the above (1) comprising a liquid absorbing member immersed in advance or upon use in the liquid formulation in which at least either of perfume or pigment is dissolved with a solvent and an evaporation carrier which is attached integrally or separately to said liquid absorbing member and which is at least partially exposed out of said retention vessel, wherein said solvent is adjusted for feeding by said liquid absorbing member and said evaporation carrier to effect evaporation, by which patterns are imparted to said evaporation carrier.

(10) The evaporation apparatus described in the above (1) comprising a liquid absorbing member immersed in advance or upon use in the liquid formulation in which at least either of a perfume or pigment is dissolved with a solvent and an evaporation carrier which is attached integrally or separately to said liquid absorbing member and which is at least partially exposed out of said retention vessel wherein said solvent is adjusted for feeding by said liquid absorbing member and said evaporation carrier to effect evaporation, by which patterns changing with the lapse of time are imparted to said evaporation carrier.

(11) The evaporation apparatus described in the above (1) comprising a liquid absorbing member to which said liquid formulation is supplied, a shield member set in such a manner that said liquid absorbing member will not contact with said liquid formulation before use and a lid member capable of fitting with said retention vessel so as to seal said opening before use, wherein said lid member is provided with a column extended into said retention vessel in which said liquid absorbing member is housed, an apical surface of said column is provided with a projection at which an aperture communicating inside said column is formed and a denticle which breaks a part of said shield member by lowering said lid member upon use, and there is a clearance between said projection and said bottom in such a state that said denticle is kept in contact with or close to the bottom of said retention vessel.

(12) The evaporation apparatus described in the above (11) wherein said projection and said denticle are placed with a clearance capable of keeping said liquid formulation by surface tension.

(13) The evaporation apparatus described in the above (11) or (12) wherein said lid member is provided with the first engagement projection and said retention vessel is also provided with the second engagement projection capable of retaining a position at which said lid member fits with said retention vessel by allowing the first engagement projection to engage therewith.

(14) The evaporation apparatus described in any one of the above items from (11) to (13) wherein said denticle is fixed so as to curve toward the direction of rotating said lid member on the above apical surface and also slanted so as to increase an extent of forward projection gradually toward the rotating direction of said lid member.

(15) The evaporation apparatus described in any one of the above items from (11) to (14), wherein a stopper is fixed which can be removed upon use while preventing said lid member from lowering before use, and the stopper is provided with a knob.

(16) The evaporation apparatus described in any one of the above items from (11) to (15), wherein said column is provided with a slit extending vertically toward said column.

In this invention, aqueous chemical compositions used in the liquid formulation usually contain glycols or other hydrophilic solvents as a solving agent together with water Glycols particularly used in this instance include ethylene glycol, propylene glycol, butylene glycol, styrene glycol, allyl glycol, butyl diglycol, isobutyl diglycol and butyl triglycol. Various chemicals conventionally used for killing insects, eliminating odors, rendering perfume, killing germs, avoidance, preventing molds, adjusting growth of plants, weeding and obtaining acaricidal effects maybe used as chemicals to be contained in the aqueous chemical composition prepared by addition of an evaporation stabilizing agent. The following show examples.

(Insecticides and Acaricides)

3-allyl-2-methylcyclopenta-2-en-4-on-1-yl d 1-cis/trans-chrysanthemate (generic name: Allethrin, trade name: Pynamin, made by Sumitomo Chemical Co., Ltd.)

3-allyl-2-methylcyclopenta-2-en-4-on-1-yl d-cis/trans-chrysanthemate (trade name: Pynamin Forte, made by Sumitomo Chemical Co., Ltd.)

d-3-allyl-2-methylcyclopenta-2-en-4-on-1-yl d-trans-chrysanthemate (trade name: Exthrin, made by Sumitomo Chemical Co., Ltd.)

3-allyl-2-methylcyclopenta-2-en-4-on-1-yl d-trans-chrysanthemate (generic name; Bioallethrin)

N-(3,4,5,6-tetrahydrophthalimide)-methyl d 1-cis/trans-chrysanthemate (generic name: Phthalthrin, trade name: Neo-Pynamine, made by Sumitomo Chemical) Co., Ltd.)

5-benzyl 3-furylmethyl d-cis/trans-chrysanthemate (generic name: Resmethrin, trade name: Crysron forte, made by Sumitomo Chemical Co., Ltd.)

5- (2-propargyl)-3-furylmethyl chrysanthemate (generic name:Furamethrin)

3-phenoxy benzyl 2,2-dimethyl-3-(2',2'-dichloro)vinylcyclopropane carboxylate (generic name: Permethrin, trade name: Eksmin, made by Sumitomo Chemical Co., Ltd.)

3-phenoxybenzyl d-cis/trans chrysanthemate (generic name: Phenothrin, trade name: Sumithrin, made by Sumitomo Chemical Co., Ltd.)

α-cyanophenoxybenzyl isopropyl-4-chlorophenyl acetate (generic name: Fenvalerate, trade name: Sumicidin, made by Sumitomo Chemical Co., Ltd.)

d-2-methyl-4-oxo-3-propargyl cyclopento-2-enyl d-cis/trans-chrysanthemate (generic name: d, d-T80-Pralethrin, trade name: Etoc, made by Sumitomo Chemical Co., Ltd.)

2,3,5,6-tetrafluoro-4-methylbenzyl-3-(2'-chloro-3',3',3'-trifluoro-1-propenyl)-2,2-dimethylcyclopropanecarboxylate (generic name: Tefluthrin)

2,3,5,6-tetrafluoro benzyl-3- (2,2-dichlorovinyl)-2,2-dimethylcyclopropanecarboxylate (generic name: Benfluthrin)

(S)-α-cyano-3-phenoxybenzyl (1R,cis)-3-(2,2-dichlorovinyl)-2,2-dimethylcyclo propane carboxylate (R,S)-8-cyano-3-phenoxy benzyl (1R,1S)-cis/trans-3-(2,2-dichlorovinyl)-2,2-dimethylcyclopropanecarboxylate α-cyano-3-phenoxybendyl d-cis/trans-chrysanthemate .1-ethynyl-2-methyl-2-bentinyl cis/trans-chrysanthemate 1-ethynyl-2-methyl-2-pentenyl 2,2-dimethyl-3-(2-methyl-1-propenyl) cyclopropane-1-carboxylate 1-ethynyl-2-methyl-2-pentenyl 2,2,3,3-tetramethylcyclopropanecarboxylate 1-ethynyl-2-methyl-2-pentenyl 2,2-dimethyl-3-(2,2-dichlorovinyl) cyclopropane-1-carboxylate O,O-dimethyl O-(2,2-dichloro)vinylphosphate O-isopropoxyphenyl methyl carbamate O,O-dimethyl O-(3-methyl-4-nitrophenyl) thionophosphate O,O-diethyl O-2-isopropyl-4-methyl-pyrimidyl-(6)-thiophosphate O,O-dimethyl-S-(1,2-dicarboethoxyethyl)-dithiophosphate The isomers are also included in the above-described compounds.

(Deodorants) (Antibromics)

These include the following: lauryl methacrylate, geranyl crotonate, myristic acid acetophenone, paramethyl acetophenone benzaldehyde, benzyl acetate, propionic acid benzyl, amylcinnamic aldehyde, anisic aldehyde, diphenyl oxide, methyl benzonate, ethyl benzonate, methyl phenylaceate, ethyl phenylacetate, neoline, safrole, cedar wood oil, cedar greens oil, citronella oil, lavandin oil, petigrain oil, lemon grass oil and others.

(Perfumes)

Natural perfumes include animal perfumes such as musk, civet and amber gris, as well as vegetable perfumes such as abies oil, ajjowan oil, almond oil, angelica root oil, basil oil, birch oil, bois de rose oil, kajabuci oil, gananga oil, capsicum, caraway oil, cardamom oil, cassia oil, celery oil, cinnamonoil, citronellaoil, cognacoil, corianderoil, cubeba oil, cumin oil, camphor oil, dilloil, estragonoil, eucalyptus oil, fennel oil, garlic oil, ginger oil, grape fruit oil, hop oil, juniperberry oil, laurel leaf oil, lemon oil, lemon grass oil, lovage oil, mace oil, nutmeg oil, mandarin oil, tangerine oil, mustard oil, peppermint oil, orange flower oil, onion oil, pepper oil, orange oil, sage oil, star anis oil, terpinene oil, wormwood oil and vanilla bean extract Artificial perfumes are either synthetic perfumes or extracted perfumes, which include hydrocarbons such as pinene and limonene; alcohols such as linalool, geraniol, citronellol, menthol, borneol, benzyl, alcohol, anise alcohol and β-phenylethyl alcohol; phenols such as anethol and eugenol; aldehydes such as n-butylaldehyde, isobutylaldehyde, hexylaldehyde, heptylaldehyde, n-nonylaldehyde, nonadienal, citral, citronellal, benzaldehyde, cinnamic aldehyde, heliotropin and vanillin; ketones such as methyl amylketone, methyl nonylketone, diacetyl, acetyl propionyl, acetyl butyryl, carvone, menthone, camphor, acetophenone, p-methyl acetophenone and ionone; lactones or oxides such as amylbutyrolactone, ethyl methylpenyl glycidate, y-nonyl-lactone, coumarin and cineol; and esters such as methylformate, isopropylformate, linalylformate, ethyl acetate, octyl acetate, menthyl acetate, benzyl acetate, cinnamyl acetate, butyl propionate, isoamyl acetate, isopropyl isobutyrate, geranyl isovalerate, allyl caproic acid, heptylbutyl, octyl capric acid, methyl heptine carboxylic acid, pelargonte ethyl, methyl octyne carboxylic acid, capric acid isoacyl, methyl laurate, ethyl myristate, ethyl benzoate, benzyl benzoate, methyl phenylacetate, butyl phenylacetate, methyl cinnamic acid, cinnamyl cinnamic acid, methyl salicylic acid, ethyl anisic acid, methyl anthranilate, ethyl pyruvate and ethyl α-butylbutyrate. Perfume may be used solely or in combination with two or more types of perfumes. Further, volatile-retaining agents such as patchouli oil, modifying agents such as eugenol or other industrial various compositions may be added together with perfumes.

(Industrial Bactericides)

Industrial bactericides include the following: 2-4,4-trichloro2'-hydroxydiphenyl ether (Irgasan DP300, made by Ciba Geigy Ltd.), 2,3,5,6-tetrachloro-4(methylsultonyl)pyridine (Dowsyl S-13, made by Dow Chemical Company), alkylbenzyldimethyl ammonium chloride (benzalkonium chloride, made by Nikko Chemicals Co. Ltd.), benzyldimethyl {2-[2-(p-1,1,3,3-tetramethylbutyl phenoxy)ethoxy] ethyl}ammonium chloride (benzethonium chloride, made by Sankyo Co., Ltd.), 4-isopropyltroboron (Hinokitiol, made by Takasago International Corporation), N,N-dimethyl-N-phenyl-N'-(fluorodichloromethylthio)sulfonamide (Prevendol A4, made by Bayer), 2-(4'-thiazolyl)benzimidazole (TBZ, made by Hokko Chemical Industry Co., Ltd.), N-(fluorodichloromethythio)-phthalimide (Prevendol A3, made by Bayer) and 6-acetoxy-2,4-dimethyl-m-dioxin (Dioxin, made by Dibordan)

(Agricultural Bactericides)

Agricultural bactericides include the following: zinc ethylenebis (dithiocarbamic acid) (Zineb, made by Rhom and Hass Company), manganese ethylenebis (dithiocarbamic acid) (Maneb, made by Rhom and Hass Company), zinc, maneb complex compound (Mancozeb, made by Rhom and Hass Company), bis (dimethyldithiocarbamic acid) ethylenebis (dithiocarbamic acid) dizinc (polycarbamate, made by TOKYO YUKIKAGAKU SHA (Tokyo Organic Chemicals Corp.)), bis (dimethyl thiocarbamoyl) disulfide (Thiram, made by Rhom and Hass Company), crotonic acid 2,6-dinitro-4-octylphenyl reactive isomer mixture (DPC, made by Rhom and Hass Company), N-trichloromethylthiotetrahydrophthalimide (Captan, made by Sankyo Co., Ltd.), 2,3-dicyano-1,4-dithiaanthraquinone (dithianone, made by Merck Ltd.), 2,4-dichloro-6-(O-chloroanilino)-S-triazine (Triazine, made by FUJIKASEIYAKUSHA (Fuji Chemical Medicine Corp.)), S-n-butyl S'-p-tertiary butylbenzyl N-3-pyridyldiocarvoneimidate (Denmart, made by Sumitomo Chemical Co., Ltd.), N-(3',5-dichlorophenyl)-1,2-dimethylchloro propane dicarboxyimide (Smilex) and bis (chlorophenyl) trichloroethanol(Kelthane), 6-methylquinoxaline-2,3-dithiocarbonate (morestan), tetrachloroisophthalonitrile (Dakonil), methyl-1-(butylcarbamoyl)-2-benzimidazole carbamate, blastcidin S-benzyl aminobenzene sulfonate, streptomycin hydrochlirde, kasugamycin hydrochloride and cycloheximide.

(Pest Insect Repellents)

Pest insect repellents include the following: dimethyl phthalate, 2,3,4,5-bis ($\Delta_2$-butylene)-tetrahydrofuran, 2,3,4,5-bis-($\Delta_2$-butylene)-tetrahydrofurfuryl alcohol, N,N-diethyl-m-triamide (DET), capric acid diethylamide, 2,3,4,5-bis-($\Delta_2$-buttlene)-tetrahydrofurfural, di-m-propyl-isocinchomeronate, secondary butylstyrylketone, nonylstyrylketone, N-propylacetate anilide, 2-ethyl-1,3-hexadiol, di-n-butylsuccinate, 2-butoxyethyl-2-furfurylden acetate, dibutyl phthalate, tetrahydrothiphene, β-naphthol, diallyldisulfide and bis(dimethylthiocarbamoyl) disulfide.

(Rodent Repellents)

Rodent repellents include tetramethylthiuram disulfite, guanidine, naphthalene cresol, cycloheximide, zinc dimethyldiocarbamate, cyclohexyl amine and N,N-dimethylsulphenyl dicarbamate.

(Dog and Cat Repellents)

Dog and cat repellents include 2,6-dimethyl-octadiene-(2,6)-al(8)(citral), O,O-diethyl S-2-ethylthioethyl dithiophosphate (ETP) and O,O-dimethyl-S-2-isopropylthioethyl dithiophosphate (MIP).

(Bird Repellents)

Bird repellents include r-chrolarose, 4-(methylthio)-3,5-xylyl-N-methylcarbamate, 4-amino pyridine anthraquinone, tetramethylthiuram disulfide and diallyldisulfide.

(Rodent Exterminating Agents)

Rodent exterminating agents include Antu, monofluoro soda acetate, warfarin, coumachlor, fumalin, coumatetralyl scillirocide, norbomide, N-3-pyridylmethyl-N'-nitrofenylurea, endrocide, alpha-naphtylthiourea, thiosemicarbazide, diphenacum, vivar, chlorophacinone, silatrane, and calciferol.

(Termicides)

Termicides include permethrin and chlordane.

(Antifungal Agents)

Antifungal agents include α-bromocinnamic aldehyde and N,N-dimethyl-N-phenyl-N'-(fluorodichloromethylthio)-sulfamide.

(Plant-growth Adjusting Agents)

Plant-growth adjusting agents include 4-chlorophenoxy acetate, gibberelin, N-(dimethylamino) succinamide and α-naphthylacetamide.

(Herbicides)

Herbicides include 2,4-D soda salt and 3,4-dichloropropionanilide.

The above chemicals can be prepared as solutions. Solvents for preparing the chemical solutions include, as explained previously, glycols such as ethylene glycol, propylene glycol, butylglycol (BG), butyldiglycol (BDG), isobutyldiglycol (BDG), butyltriglycol (BTG), styrene glycol and allyl glycol. Lower alcohols may be used similarly as the above solvents from a technological point of view, because they help the chemicals to dissolve. The solvent solution to be used in the above chemicals is prepared usually at a chemical concentration of about 0.2 to 20% by weight and preferably at a concentration of 0.5 to 10 % by weight. The evaporation stabilizing agent is added at the previously described ratio to an aqueous solution to prepare a liquid formulation.

The following chemicals may be added to the chemical solution for the purpose of improving and adjusting the solubility of the solution or the evaporation upon heating.

3,5-di-t-butyl-4-hydroxytoluene (hereinafter referred to as BHT)

3-t-butyl-4-hydroxyanisole.3,5-di-t-butyl-4-hydroxy anisole.mercaptobenzoimidazole. dilauryl-thio-di-propionate. 2,2'-methylene-bis-(6-t-butyl-4-methylphenol)

2,2'-ethylene-bis-(6-t-butyl-4-ethyl phenol)

4,4'-methylene-bis-(2,6-di-t-butyl-phenol)

4,4'-butylidene-bis-(6-t-butyl-3-methylphenol)

4,4'-thio-bis-(6-t-butyl-3-methylphenol)

1,1-bis-(4-hydroxyphenyl)cyclohexane 1,3,5-trimethyl-2, 4,6-tris (3,5-di-t-butyl-4-hydroxybenzyl)benzene. tris (2-methyl-4-hydroxy-5-t-butylphenyl)butane. tetrakis [methylene(3,5-di-t-butyl-4-hydroxyhydrocinnamate)] methane octadecyl-3,5-di-t-butyl-4-hydroxyhydroxinnamate Phenyl-β-naphtylamine. N,N-diphenyl-p-phenylenediamine.2,2,4-trimethyl-1,3-dihydroquinoline polymer. 6-ethoxy-2,2,4-trimethyl-1,3-dihydroquinoline.2-t-butyl-4-methoxyphenyl.3-t-butyl-4-methoxyphenol.2,6-di-t-butyl-4-ethylphenol. stearyl-β-(3,5-di-t-butyl-4-hydroxyphenyl)propionate. α-tocopherol ascorbic acid and erythorbic acid.

The above chemicals may be used solely or in combination with two or more types of them. They are used preferably at about 0.001 to 2.0% by weight in relation to the chemical solution added to an evaporation stabilizing agent of the invention, and more preferably at about 0.01 to 1.0% by weight.

The above liquid absorbing member used in the invention usually includes any materials such as felt, cotton, pulp, non-woven cloth, asbestos and inorganic substance-forming materials, and preferably includes felt core, biscuit core, pulp core and inorganic substance-forming core.

Examples of the above inorganic-substance forming cores include those prepared by solidifying inorganic fibers such as porous porcelain, glass fiber and asbestos with a binder such as gypsum or bentonite or those prepared by solidifying solely or in combination with mineral powders such as kaolin, activated white clay, talc, diatomaceous earth, clay, perlite, bentonite, alumina, silica, alumina silica, titanium, vitric volcanic rock calcination powder and vitric volcanic ash calcination powder, together with wood powder, carbon powder or activated carbon, with a paste, for example, dextrin, starch, gum arabic or synthetic paste (CMC). The above mineral powders (100 parts by weight) and wood powder alone or wood powder mixed with an equal quantity of carbon powder and/or activated carbon (10 to300parts by weight) are blended with a paste in a quantity of 5 to 25% by weight in relation to a total weight of the liquid absorbing member, to which water is added, and the resultant is kneaded, subjected to extrusion molding and drying to obtain particularly preferable liquid absorbing cores. An oil-absorbing velocity of said liquid absorbing member is preferably 1 to 40 hours and more preferably 8 to 21 hours. The oil-absorbing velocity is a value obtained by immersing a liquid absorbing core 7 mm diameter and 70 mm long in n-paraffin solution at 25° C. up to a point of 15 mm from the bottom to determine the time when n-paraffin reaches the core. The above liquid absorbing core may contain, whenever necessary, pigments such as malachite green, sorbic acid and its salts and antifungal agents such as dehydroacetic acid, together with the above mineral powder, wood powder and pastes.

Any aqueous or oil-based pigments may be used, as long as they are non-volatile and soluble in solvents. Such pigments include, for example, synthetic pigments (Red No. 102, Red No. 225, Blue No. 1, Yellow No. 4 etc.).

Since the above-explained evaporation apparatus is able to adjust the evaporation of active ingredients by the adjusting means, active ingredients contained in the liquid formulation can be prevented from evaporation before use. Adjusting active ingredients so as to evaporate in a necessary and sufficient quantity upon use makes it possible to keep the effect of active ingredients for a long period.

According to the evaporation apparatus described in the above item (2), when users rotate the rotating part of the apparatus to communicate with the inner opening with the outer opening, active ingredients of the liquid formulation contained in the exposed liquid absorbing member will evaporate from the evaporation apparatus. Thus, if the apparatus is kept in such a state that the inner opening and the outer opening are not communicated before use, the active ingredients can be prevented from evaporation. The evaporation apparatus can keep the effect of the active ingredients for a prolonged time.

The evaporation apparatus of the above item (3) is desirable in that it has a clip connection and a clip having plural tightening parts, the one end of which is held with said clip connection wherein other ends of said tightening parts are tightened to each other to provide an irregular surface on the contacting part. Thus, such an evaporation apparatus can be easily attached to a louver of an air conditioner in a car or in a room by using the clip. The irregular surface provided on the tightening parts of the clip is helpful in fixing more firmly the evaporation apparatus to the louver of an air conditioner. In addition, since plural tightening parts are provided at the sites opposite those to be tightened integrally by the clip connection, tightening parts of the clip will not be removed from the clip to prevent them from falling upon fixing.

The evaporation apparatus described in the above item (4) is available, with the clip removed from the outer vessel, thus making it possible to pack the evaporation apparatus in a smaller container at each stage of manufacture, transportation and others.

According to the evaporation apparatus described in the above item (5), it is possible that a part is erected from the body of the evaporation carrier to increase a surface area of the evaporation carrier for evaporation, by which active ingredients contained in the liquid formulation can be more effectively evaporated than a case where the erected part is not provided.

According to the evaporation apparatus described in the above item (6), it is possible that the liquid formulation housed in the retention vessel is supplied through the liquid absorbing member to the evaporation carrier, so that the liquid formulation is supplied in a more quantitative manner to the evaporation carrier and therefore active ingredients in the liquid formulation can be evaporated in a more stable manner from the evaporation carrier.

According to the evaporation apparatus described in the above item (7) it is possible that where the evaporation carrier is made with porous materials to give an area of 32 mm$^2$ and the thickness of 5 mm, the liquid absorption quantity in about 50 minutes in said evaporation carrier exceeds 7.5 g, thus making it possible to keep a sufficient quantity of the liquid formulation in the evaporation carrier and consequently to evaporate active ingredients contained in the liquid formulation sufficiently and stably.

According to the evaporation apparatus described in the above item (8), the liquid absorbing member contacts with the evaporation carrier on the surface, so that the liquid formulation can be supplied in an almost constant quantity through the liquid absorbing member to the evaporation carrier. Such a configuration that allows the liquid absorbing member and the evaporation carrier to contact on the surface could always supply the liquid formulation through the liquid absorbing member to the evaporation carrier in a larger quantity than the supply on a point contact or a line contact. Therefore, the evaporation apparatus described in the invention makes it possible to evaporate active ingredients contained in the liquid formulation sufficiently and stably.

According to the evaporation apparatus described in the above item (9), the liquid formulation is supplied from the liquid absorbing member to the evaporation carrier, by which the evaporation carrier can change in colors or patterns. Thus, it is possible not only to adjust a state of the evaporation in the evaporation apparatus by visual checks but also to improve decorative features of the evaporation apparatus upon appreciation of the apparatus set at a desired area in a room.

In addition, the evaporation apparatus described herein can offer users an enjoyment of decorative change in a shorter time, as compared with conventional evaporation apparatuses, providing a sufficient visual stimulation to prevent users from being bored.

According to the evaporation apparatus described in the above item (10), besides the similar effect provided by the evaporation apparatus of the above item (9), users are able to enjoy change in colors or patterns of the evaporation carrier, with the lapse of time, and decorative features are further improved.

According to the evaporation apparatus described in the above item (11), users are able to lower the lid member, whenever necessary, to break said shield member by the denticle formed on the apical surface of the column on the lid member, by which the liquid formulation housed in the retention vessel is supplied from the aperture of the projection on the column into the column. The thus supplied liquid formulation is then absorbed by the liquid absorbing member provided inside the column. Active ingredients of the liquid formulation absorbed by the liquid absorbing member are evaporated into the ambient atmosphere outside the evaporation apparatus.

In addition, the above-mentioned projection will not contact with the above-mentioned retention vessel upon lowering the above-mentioned lid member, thus making it possible to smoothly flow the liquid formulation into the aperture of the projection and also to smoothly absorb the liquid formulation inside the retention vessel until the very last.

The above evaporation apparatus is able to prevent contact of the liquid absorbing member with the liquid formulation before use, as a result of the shield member. In addition, the evaporation apparatus is free of the necessity of such troublesome work that users must remove the shield member from the retention vessel and again fix the lid member to the retention vessel upon use so that liquid absorbing member can contact with the liquid formulation, and therefore provide more convenience. In this instance, the liquid formulation will not adhere to the hands of users.

The apparatus is also free from the necessity of removing the lid member from the retention vessel, thereby preventing the liquid formulation from leakage from the evaporation apparatus.

Further, since turning the lid member upon use makes it possible to break the shield member, users do not need to apply a greater force thereto than in a case where the shield member is just broken vertically.

In addition, there is no need to provide a so-called disposable cap which is taken off of the evaporation apparatus and disposed before use, which makes it possible to reduce the number of parts to be used in the evaporation apparatus.

Furthermore, the apparatus can be easily assumed for usage during distribution and packed in a smaller container.

According to the evaporation apparatus described in the above item (12), where only a small quantity of the liquid formulation is left, the liquid formulation contained in the retention vessel can be kept by surface tension by means of the projection and the denticle on the apical surface of the column, and the thus kept liquid formulation is supplied through the aperture of the projection into the column. Therefore, even where only a small quantity of the liquid formulation is left, active ingredients may be smoothly absorbed by the liquid absorbing member.

According to the evaporation apparatus described in the above item (13), engaging the first engagement projection together with the second engagement projection makes it possible to keep the lid member in such a state that it fits with the retention vessel, for example, where no stopper is provided during the manufacturing process, thus preventing the lid member from an accidental turn. Namely, it is possible to prevent the lid member from being removed from the retention vessel due to vibrations during distribution.

According to the evaporation apparatus described in the above item (14), turning and lowering the lid member makes it possible that the denticle breaks the shield member, cutting apart a desired part of the shield member, and dividing the shield member so that the liquid formulation can flow into, thus, allowing the liquid formulation contained in the retention vessel to flow smoothly.

According to the evaporation apparatus described in the above item (15), users are able to pull out a knob, whenever necessary, to remove the stopper.

According to the evaporation apparatus described in the above item (16), where the shield member is broken upon use, the liquid formulation housed in the retention vessel flows into the column not only from the aperture of the projection but also from the slit, thus, making it possible to absorb the liquid formulation more smoothly.

BRIEF DESCRIPTION OF THE DRAWINGS

FIG. 20 is an overall perspective view of the stopper shown in FIG. 15.

BEST MODE FOR CARRYING OUT THE INVENTION

A detailed explanation will be made hereinafter for the embodiments of the evaporation apparatus of the present invention on the basis of the drawings. It shall be however, interpreted that the evaporation apparatuses of the invention shall not be restricted by these embodiments.

First Embodiment

Figure 1:
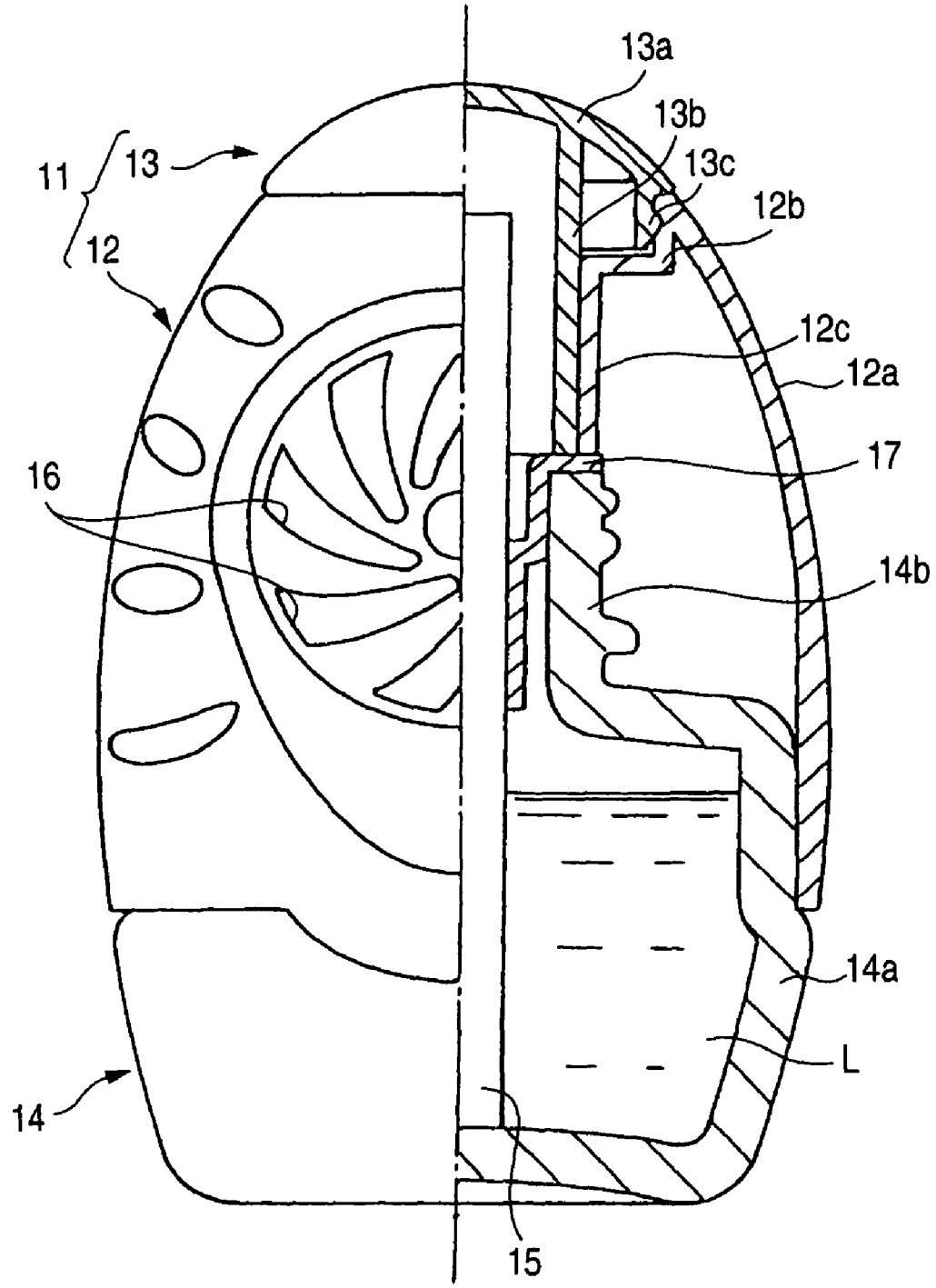
FIG. 1 is a front view including a partial cross-sectional view showing the first embodiment of the evaporation apparatus in the present invention.

As shown in FIG. 1, an evaporation apparatus 10 of this invention is provided with a retention vessel 14 which houses a liquid formulation L and an outer vessel 11 fixed on the upper part of the retention vessel 14. The retention vessel 14 is configured with the body of a vessel 14a which houses the liquid formulation L and an opening 14b fixed on the upper part of the body of the vessel 14a. The opening 14b is a cylindrical projection and configured so as to link with the body of the vessel 14a at the lower inner circumferential part.

A liquid absorbing core 15 which acts as the liquid absorbing member is inserted through the opening 14b on the retention vessel 14, one end of which is immersed in the liquid formulation L contained in the retention vessel 14 and the other end of which is exposed out of the retention vessel 14. One end of the liquid absorbing core 15 is provided so as to keep in contact with or close to the bottom of the retention vessel 14. The liquid absorbing core 15 is fixed and supported with a supporting lid 17 fitted with the inner circumference of the opening 14b.

The outer vessel 11 is configured with a trunk 12 fixed so as to cover an exposed part of the liquid absorbing core 15 and a head 13 fixed above the trunk 12. The head 13 is configured with a dish-like rotating part 13a, cylindrical inner cylinder 13b projected downward from the center of the rotating part 13a and an outer cylinder 13c projected downward from the edge of the rotating part 13a. The lower end of the inner cylinder 13b is kept in contact with or close to the upper end of the opening 14b on the retention vessel 14.

The trunk 12 is configured with a trunk body 12a, an upper opening 12b formed on the upper part of the trunk body 12a so as to fit with the outer cylinder 13c of the head 13, and an inner cylinder 12c formed in a smaller diameter than that of the upper opening 12b and coaxially. The trunk 12 is positioned so that the inner cylinder 12c slides with an outer circumference of the inner cylinder 13b of the head 13 or keeps a slight clearance with the outer circumference. The trunk 12 is provided with plural evaporation apertures 16 for allowing active ingredients of the liquid formulation L to diffuse out of the evaporation apparatus 10.

The exposed end of the liquid absorbing core 15 (upper end as indicated in FIG. 1) is placed on the inner circumference of the inner cylinder 13b of the head 13.

Figure 2:
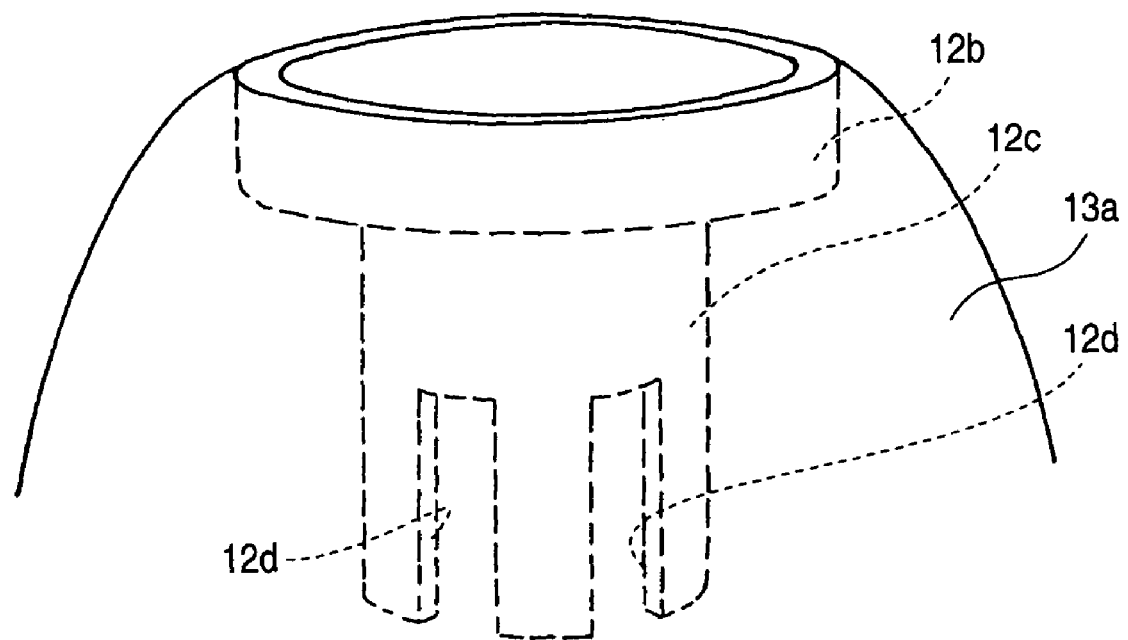
FIG. 2 is an enlarged view of the inner cylinder of the head and the inner cylinder of the trunk.

As shown in FIG. 2, the lower end of the inner cylinder 13b of the head 13 is provided with plural evaporation openings 13c at intervals in a circumferential direction.

Further, the inner cylinder 12c of the trunk 12 is provided with plural evaporation openings 12d at intervals in a circumferential direction. The plural evaporation openings 13c and 12d are available in a slit configuration, for example.

As shown in FIG. 1 and FIG. 2, in the evaporation apparatus 10 of this embodiment, the head 13 is mounted on the trunk 12 in an axial-rotatable manner, with the liquid absorbing core 15 as the center of rotation. Rotation of the head 13 makes it possible to turn around the inner cylinder 13b, by which the evaporation opening 13c can move to a position which allows it to communicate with the evaporation opening 12d of the inner cylinder 12c on the trunk 12.

In this embodiment, there is no restriction on the configuration of the evaporation openings 13c and 12d. The evaporation openings 13c and 12d are available in configuration which can adjust a mutually communicating area, according to the rotation of the head 13. Thus, the evaporation apparatus 10 can adjust the quantity of evaporated active ingredients.

Figure 3:
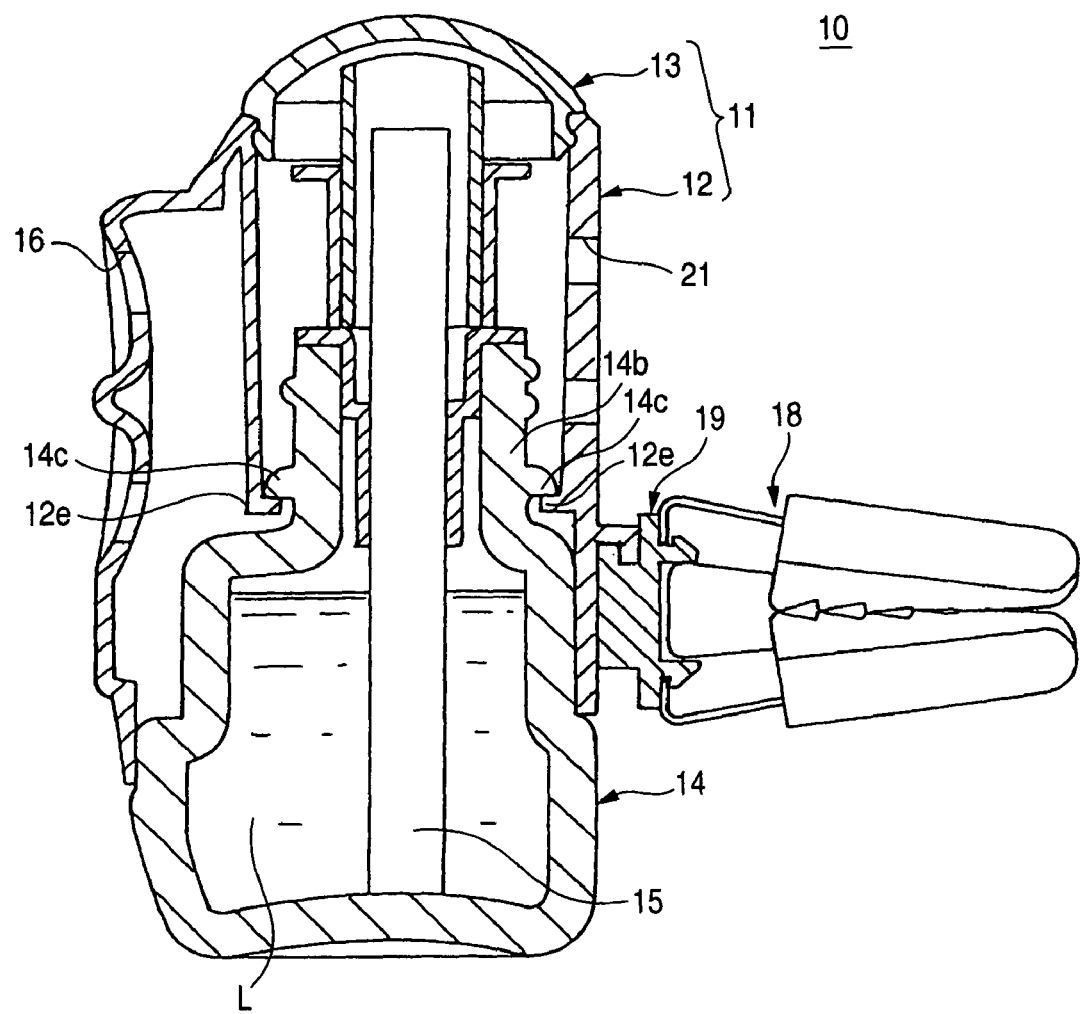
FIG. 3 is a side cross-sectional view of the evaporation apparatus shown in FIG. 1.

As shown in FIG. 3, in the evaporation apparatus 10 of this embodiment, the opening 14b of the retention vessel 14 is provided with a flange 14c. Further, a nail 12e is formed inside the trunk 12. The outer vessel 11 can be firmly fixed to the retention vessel 14 by allowing the nail 12e to engage with the flange 14c at the opening 14b of the retention vessel 14. The flange 14c is available in any configuration as long as it can engage with the nail 12e.

The trunk 12 is provided with an evaporation aperture 21 on desired sites opposite the evaporation aperture 16. Thus, air distributed from air conditioners installed in a car or in a room, which is not illustrated here, can be taken into the evaporation apparatus 10 through the evaporation aperture 21, thus allowing active ingredients to evaporate more effectively.

In addition, as shown in FIG. 3, the trunk 12 of the evaporation apparatus 10 in this embodiment is provided with a clip 18 via an attaching part 19.

Figure 4:
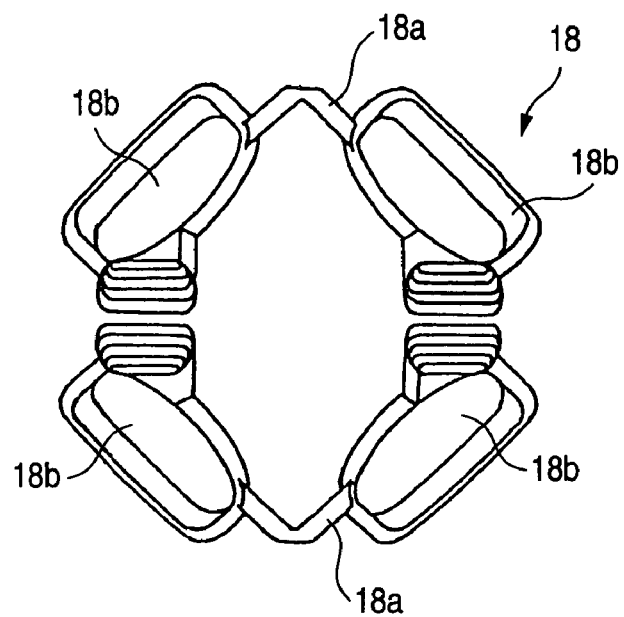
FIG. 4 is a drawing showing a state of the clip when viewed from the front edge.

FIG. 4 is a drawing of the clip 18 shown in FIG. 3, when viewed from the front edge (right side in FIG. 3).

As shown in FIG. 3 and FIG. 4, the clip 18 has a clip connection 18a and plural tightening parts 18b (4 in this embodiment) one end of which is retained with said clip connection 18a. In this embodiment, provided are two clip connections 18a, each of which is provided with two tightening parts 18b. These two clip connections 18a are mutually mated so as to form an approximate square when FIG. 4 is viewed at the front. Here, the clip connections 18a are configured with a fitting having a predetermined elastic stress such as metal. The tightening parts 18b are formed integrally with the clip connection 18a at one end and formed with resin covering a part of the clip connection 18a at the other end. The clip 18 is configured so as to effect mutual tightening based on elastic stress by the tightening parts 18b as shown at the upper and lower parts in FIG. 4.

Figure 5:
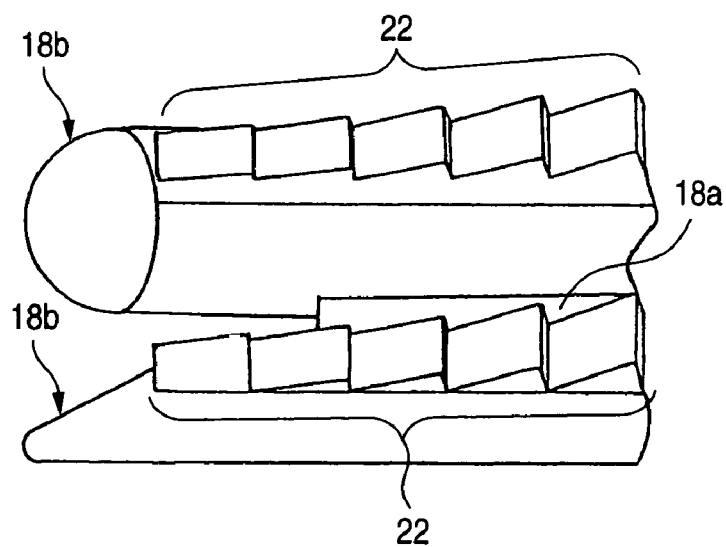
FIG. 5 is an enlarged view of the edge of the clip.

As shown in FIG. 5, the tightening parts 18b of the clip 18 are provided with irregular surfaces 22 at a site where other ends are mutually tightened and contacted. The clip 18 configured according to this embodiment can be fixed to be a vertical or horizontal louver of the air conditioner installed in a car or in a room, which is not illustrated here. The louver can be kept between the irregular surfaces 22 formed individually on the tightening parts 18b which are tightened to each other, by which the clip 18 can be firmly fixed to the louver.

The clip connection 18a is provided in an attachable and detachable manner via the attaching part 19 on the back of the outer vessel 11 (left and outside the trunk 12 in FIG. 3). Inserting the attaching part 19 into a projection formed on the trunk 12 allows to fix the clip 18 to the outer vessel 11. In this instance, the projection is formed so as to give an approximate rectangle when viewed from the right in FIG. 3, and can be inserted into the attaching part 19 formed in a rectangle so as to accept the projection. However, a projection may be formed to give an approximate square in such a way that the clip 18 can be turned at 90 degrees when viewed from the right in FIG. 3.

The attaching part 19 may be attached to the outer vessel in a freely rotating manner (clock-wise or counter clock-wise rotation when viewed from the right in FIG. 3). Such attachment makes it possible to move the clip connection 18a and the tightening parts 18b on the clip 18 vertically or horizontally according to the position of the louver, so that the clip 18 can be attached to a wide variety of louvers. Further, the tightening parts 18b may be available as a pair of right and left or up and down parts, and not restricted in configuration or the number described in the above.

In the evaporation apparatus 10 of this embodiment, the liquid formulation L is absorbed upward by the liquid absorbing core 15 to reach at the exposed end of the liquid absorbing core 15. In this instance, since the exposed end of the liquid absorbing core 15 is covered with the inner cylinder 13b of the head 13, the thus absorbed active ingredients contained in the liquid formulation L will not be evaporated out of the evaporation apparatus 10. When users rotate the rotating part 13a of the head 13 upon use, the inner cylinder 13b of the head 13 and the inner cylinder 12c of the trunk 12 are mutually rotated to result in respective communicate with the evaporation openings 13c and 12d. Then, active ingredients of liquid formulation L absorbed by the liquid absorbing core 15 are diffused out of the evaporation apparatus 10 through the evaporation openings 13c and 12d as well as the evaporation apertures 16 and 21. Therefore, the evaporation apparatus 10 will not evaporate active ingredients before use and also can evaporate them only in a necessary quantity, thereby keeping active ingredients effective for a longer time.

In this embodiment, the site immersed into the liquid formulation L of the liquid absorbing core 15 acts as a liquid absorbing mechanism, while the exposed site acts as an evaporation mechanism. Further, the inner cylinder 13b of head 13 and the inner cylinder 12c of the trunk 12 are rotated, thus allowing the respective evaporation openings 13c and 12d to communicate, the mechanism of which acts as an adjusting means for evaporation of active ingredients.

Further, in this embodiment, the inner cylinder 13b of head 13 acts as an inner member, the inner cylinder 12c of the trunk 12 acts as an outer member, and the respective evaporation openings 13c and 12d of the inner cylinder 13b and 12c act as the respective inner openings.

In other words, in this embodiment, the evaporation apparatus comprises a liquid absorbing member, at least a part of which is exposed out of said retention vessel, a cylindrical inner member positioned so as to cover an exposed site of said liquid absorbing member, a cylindrical outer member positioned so as to cover said inner member and a rotating part fixed to said inner member or said outer member, wherein said inner member is provided with an inner opening, said outer member is provided with an outer opening and rotation of said rotating part allows said inner opening and said opening to communicate, by which said liquid absorbing member is exposed to evaporate active ingredients.

The following shows an example of the liquid formulation used in the evaporation apparatus of this embodiment. In the following example, ultraviolet-ray absorbing agents include benzophenone, diphenyl cyano acrylate, triazine, and p-aminobenzoic acid mixture, which shall be similarly applied to the subsequent embodiments. Solvents include dipropylene glycolmonomethyl ether and others explained previously.

| (Ingredients) | (Quantity) |
| --- | --- |
| Perfume (odor control agent) | 50.0 g |
| Lauryl methacrylate (deodorant) | 0.1 g |
| Eucalyrtol(antibacterial agent) | 0.1 g |
| Ultraviolet ray absorbing agent | 0.1 g |
| Pigment (coloring agent) | 0.1 g |
| Solvent | adequate quantity |
| (Total) | 100 g |

Second Embodiment

Figure 6:
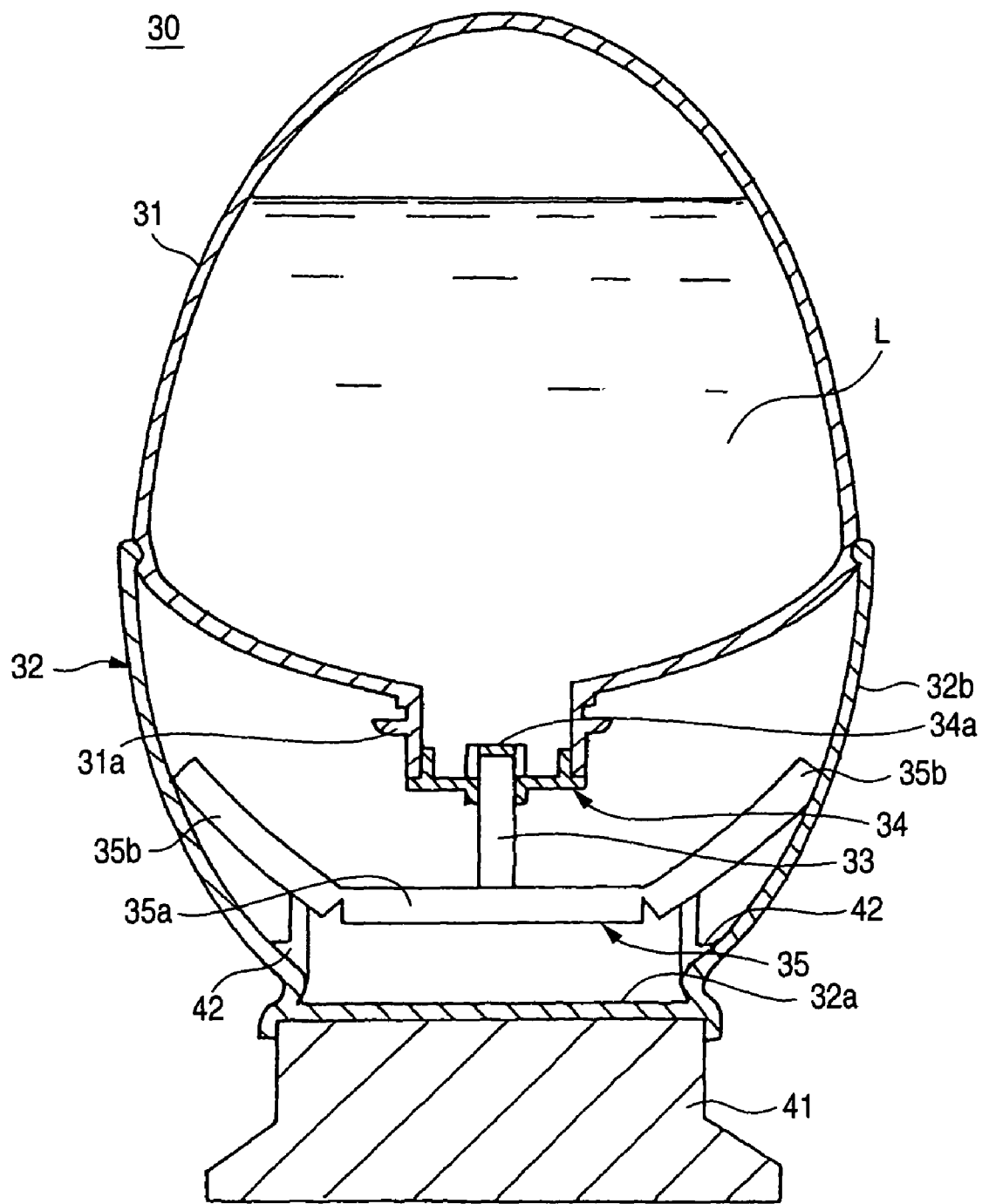
FIG. 6 is a cross-sectional view showing the second embodiment of the evaporation apparatus in the invention.
Figure 7:
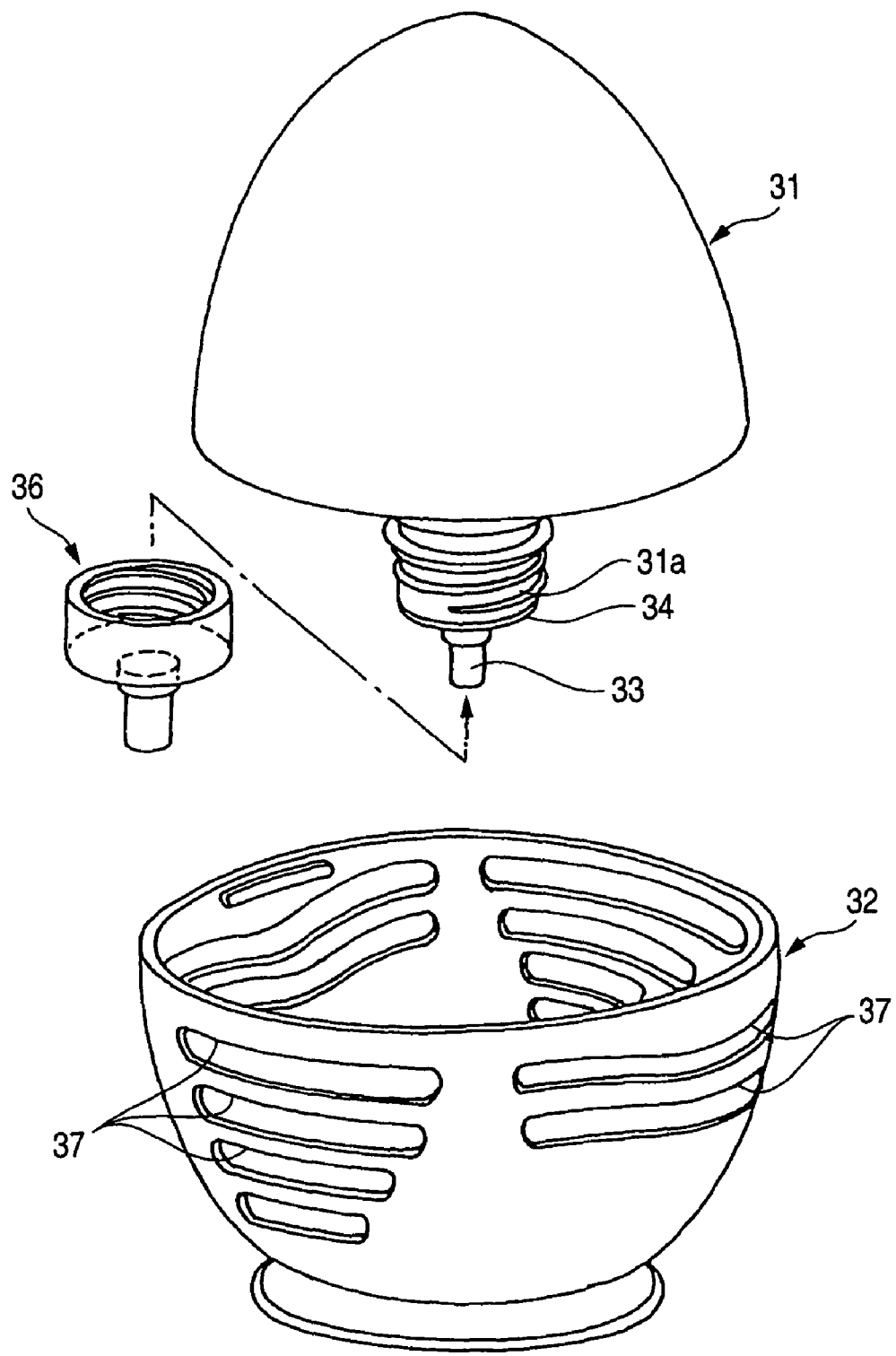
FIG. 7 is an exploded perspective view of the evaporation apparatus shown in FIG. 6.

As shown in FIG. 6 and FIG. 7, an evaporation apparatus (hereinafter referred to as evaporation apparatus) 30 is an inverted-type evaporation apparatus comprising a retention vessel 31 housing the liquid formulation L in which active ingredients are contained and an outer vessel 32 supporting the lower side of a retention vessel 31. The outer vessel 32 is simply configured by having a bottom wall 32a and a circumferential wall 32b. As shown in FIG. 7, the circumferential wall 32b of outer vessel 32 is provided with evaporation aperture 37.

An opening 31a is provided at the lower part of the retention vessel 31. The opening 31a is projected into the lower part of the retention vessel 31 in a cylindrical manner. The retention vessel 31 is communicated inside out via the opening 31a.

The lower end of the opening 31a is closed with the plug 34. The concaved part 34a at the center of the plug 34 is fitted with a column-shaped liquid absorbing member 33. The liquid absorbing member 33 acts as a liquid absorbing member. The liquid absorbing member 33 is exposed downward from the retention vessel 31. The apical surface at the lower part of the liquid absorbing member 33 (the part exposed from the retention vessel 31) is formed to give a flat surface. The base 41 is provided for supporting the bottom wall 32a of the outer vessel 32 from the underneath.

As shown in FIG. 7, the outer circumferential surface of the opening 31a is provided with screw threads and a cap 36 configured so as to fit with these threads is fixed to cover the liquid absorbing member 33 and the plug 34 before use.

As shown in FIG. 6, the evaporation carrier 35 is provided above the bottom wall 32a of the outer vessel 32, and configured so as to allow the apical surface of the liquid absorbing member 33 to contact with the flat upper surface of the evaporation carrier 35 on the surface.

The circumferential wall 32b of the outer vessel 32 is provided with plural evaporation aperture 37.

In this embodiment, since the liquid absorbing member 33 is configured so as to contact with the evaporation carrier 35 on the surface, the liquid formulation L supplied to the evaporation carrier 35 via the liquid absorbing member 33 can be kept always in a larger quantity than in a case where the liquid absorbing member 33 is configured to contact with the evaporation carrier 35 on a point or on a line. Thus, the evaporation apparatus 30 can evaporate active ingredients contained in the liquid formulation L sufficiently and stably.

As explained above, it is preferable that the retention vessel 31 supported by the outer vessel 32 is positioned in such way that the liquid absorbing member 33 is allowed to contact with the evaporation carrier 35 on the surface. It is preferable that, for example, the evaporation apparatus 30 has a part for retaining the liquid absorbing member 33 or the retention vessel 31 so that the liquid absorbing member 33 is allowed to contact with the evaporation carrier 35 on the surface.

The liquid formulation L stored in the retention vessel 31 is absorbed by the liquid absorbing member 33 and moved by gravity toward the lower front edge of the liquid absorbing member 33, and the liquid formulation L is permeated into the evaporation carrier 35 from the lower front edge of the liquid absorbing member 33. Then, active ingredients of liquid formulation L evaporated from the evaporation carrier 35 are diffused out of the evaporation aperture 37 provided on the outer vessel 32.

Figure 8:
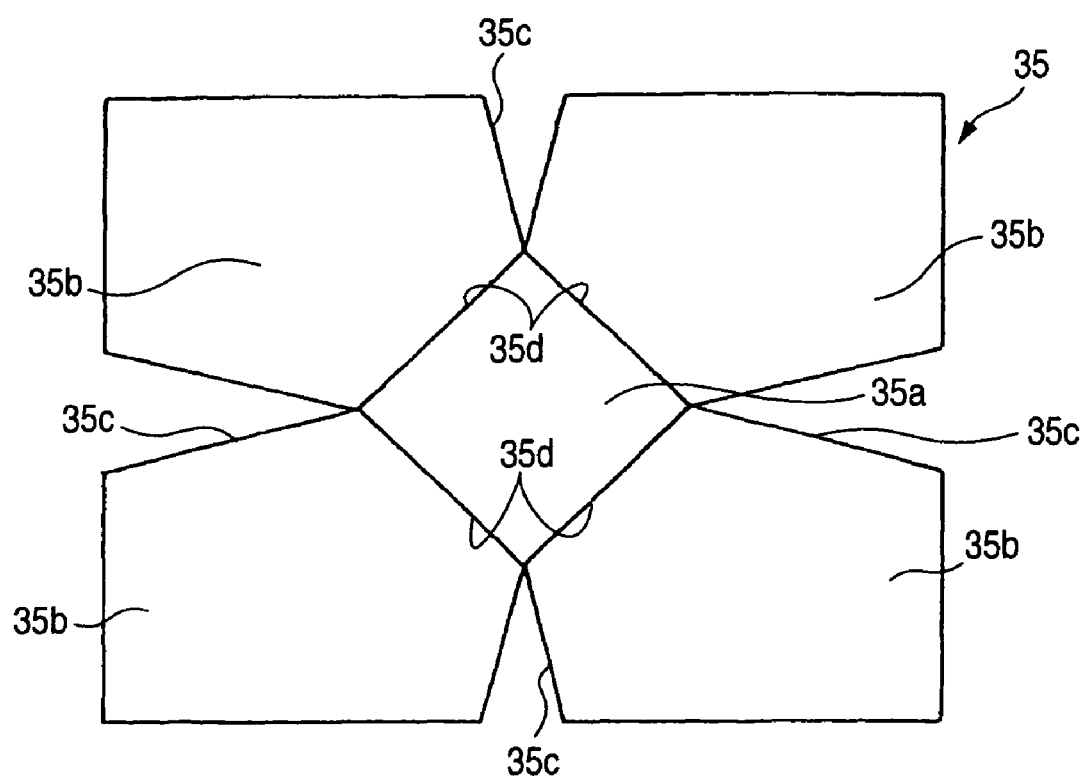
FIG. 8 is a drawing showing a state of the evaporation carrier before housed in the outer vessel.

FIG. 8 shows a state of the evaporation carrier 35 before being housed in the outer vessel 32. The evaporation carrier 35 is configured with a body 35a and a part 35b erected from the body 35a. The evaporation carrier 35 is made with layers of non-woven cloth in a rectangular form. It is preferable that the evaporation carrier 35 has about a 2 to 10 mm-thick layer of non-woven cloth.

As shown in FIG. 8, the evaporation carrier 35 is provided with notches 35c at the center of individual sides of an approximate rectangle. Grooves 35d are provided on the lower surface of the evaporation carrier 35 (the surface opposite the bottom wall 32a of the outer vessel 32) so as to connect these notches 35c. Although these grooves 35d may not be provided, it is preferable that the grooves 35d are provided for example, where the evaporation carrier 35 is made with non-woven cloth, with the thickness exceeding 5 mm. It is desirable that the grooves 35d are formed by a notch, compression (press), dotted line, etc., and the erected part 35b can be easily prepared. The evaporation carrier 35 as a whole of or the erected part 35b alone may be rendered thinner to omit the thread.

The groove 35d is preferably about 0.5 to 5 mm in width. A square area enclosed with the grooves 35d is provided as the body 35a, and a pentangular area outside the grooves 35d is provided as the erected part 35b. In this instance, the body 35a and the erected part 35b are made with the integral member.

Figure 9:
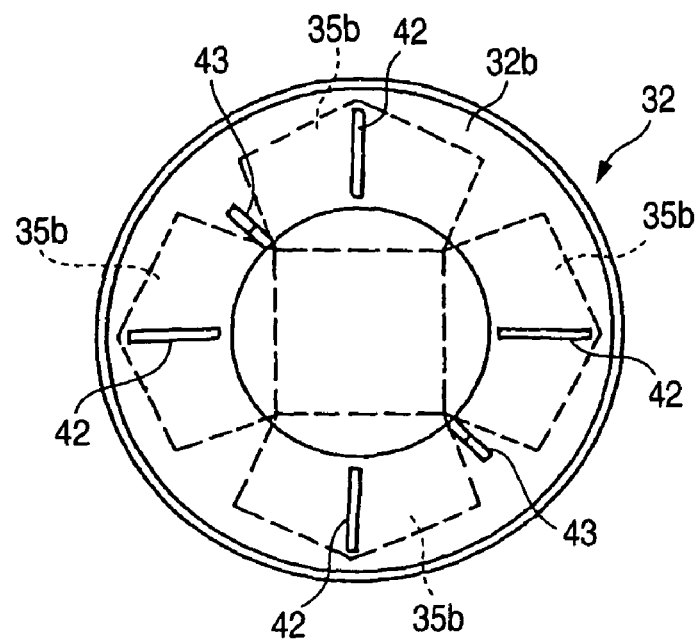
FIG. 9 is a top view showing a state of the evaporation carrier housed in the outer vessel.

As shown in FIG. 9, the evaporation carrier 35 is housed into the outer vessel 32. In this instance, erected part 35b is erected as shown in FIG. 6. Since the notched part 35c is provided, the adjacent erected parts 35b will not interfere with each other to attain a smooth erection.

In addition, as shown in FIG. 9, four supporting pieces 42 provided at the lower side of the circumferential wall 32b of outer vessel 32, in a state where the evaporation carrier 35 is housed into the outer vessel 32, individually support upward the erected part 35b of the evaporation carrier 35, thereby keeping the erected position against the body 35a of erected part 35b. Further, the circumferential wall 32b is provided with a pair of partitioning walls 43, each of which is positioned at a site corresponding to the notch 35c. Therefore, the evaporation carrier 35 can be prevented from an accidental movement inside the outer vessel 32.

Figure 10:
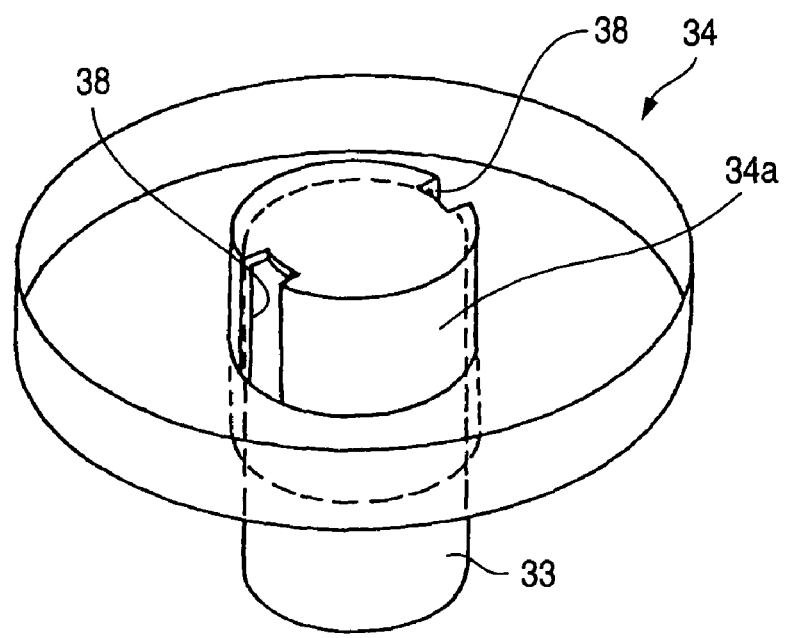
FIG. 10 is an enlarged perspective view of the plug shown in FIG. 6.

As shown in FIG. 10, the plug 34 is provided with plural slits 38 at the concaved parts 34a. The concaved part 34 is configured so that the liquid absorbing member 33 is exposed inside the retention vessel (at the upper part in FIG. 10) from an opened area of the slit 38. There is no particular restriction on the number and configuration of the slit 38.

The liquid formulation L is supplied quantitatively to the evaporation carrier 35 via the liquid absorbing member 33 from the retention vessel 31.

The evaporation carrier 35 provided on the above-configured evaporation apparatus 30 is made with porous materials and configured so that the foregoing evaporation carrier can attain a liquid absorption quantity exceeding 7.5 g after 50 minutes when the carrier has an area of 32 mm$^2$ and a thickness of 5 mm (namely, volume of 160 mm$^3$).

The evaporation apparatus 30 is also configured so that the evaporation carrier 35 can be 0.15 to 0.25 g/cm$^3$ in density.

According to the thus configured evaporation carrier 35, the liquid formulation L contained in the liquid absorbing member 33 can be diffused and retained over all the evaporation carrier 35 and active ingredients contained in the liquid formulation L can be effectively diffused.

The evaporation carrier 35 used in the evaporation apparatus shown in FIG. 6 was subjected to the following test to confirm variation in the quantity of the liquid formulation L retained (quantity of the liquid absorbed) depending on the difference in the density.

The following aromatic deodorant (200 ml) was placed in a 220 ml-capacity glass-made retention vessel, the opening of which was closed with a rubber stopper (stopper). The rubber stopper was penetrated with a column-shaped core which acts as a liquid absorbing member. The core used in this test was made with polyethyleneterephthalate (PET).

Prescription of aromatic deodorant (liquid formulation)

| (Ingredients) | (Quantity) |
| --- | --- |
| Ethanol | 10.0 g |
| Anion surfactant | 3.0 g |
| Nonion surfactant | 7.0 g |
| Lemon perfume | 8.0 g |
| Yellow No. 4 | 0.1 g |
| Purified water | adequate |
| (Total) | 200.0 ml |

Evaporation carriers used in the test were those with a density of 0.13 g/cm$^3$ (hereinafter referred to as Sample 1), those with 0.2 g/cm$^3$ (hereinafter referred to as Sample 2) and those with 0.28 g/cm$^3$ (hereinafter referred to as Sample 3). Evaporation carriers used in the test were all those made mainly with pulp materials, with a rectangular configuration, area of 32 mm$^2$ and thickness of 5 mm. Liquid formulation was supplied to these evaporation carriers through liquid absorbing members from the above vessel to determine a quantity of the liquid retained (a quantity of the liquid absorbed (g)) respectively for the Sample 1, Sample 2 and Sample 3, with the lapse of time.

The following table shows the results of this test.

TABLE 1

Results of the test

| Evaporation carrier | Density (g/cm³) | Quantity of the liquid absorbed after 50 minutes | Quantity of the liquid absorbed after 90 minutes | Quantity of the liquid absorbed after 120 minutes |
|---|---|---|---|---|
| Sample 1 | 0.13 | 4.5 | 6.8 | 7.5 |
| Sample 2 | 0.20 | 7.5 | 12.4 | 13.0 |
| Sample 3 | 0.28 | 2.8 | 2.8 | 2.8 |

The above test revealed that the Sample 2 was able to absorb the liquid in the greatest quantity and proved excellent as an evaporation carrier for an inverted-type evaporation apparatus. In contrast, the Sample 1 with the lowest density and the Sample 3 with the highest density were found to be lower in the liquid-absorption quantity than the Sample 2.

The results confirmed that the liquid absorption quantity and the density in relation to the area and thickness were important factors for an evaporation carrier.

Next, a polyacryl (PA) core was used as a core for the liquid absorbing member to conduct a similar test as described above. The Sample 2 was used as an evaporation carrier in which the upper surface was 60 cm².

In this test, the liquid absorption quantity (g) was checked for the evaporation carrier every 60 minutes. The results are shown in Table 2.

TABLE 2

Results of the test

| | Time (minute) | | | |
|---|---|---|---|---|
| | 0 | 60 | 120 | 180 |
| Absorption liquid quantity (g) | 0 | 15.61 | 24.04 | 26.06 |

As apparent from the results shown in Table 2, even core material as PA, when the area and the thickness were respectively 32 mm² and 5 mm (namely, 160 mm³ in the volume) and the above-mentioned evaporation carrier exhibited a liquid absorption quantity exceeding 7.5 g after 50 minutes, the liquid absorption quantity was increased and the liquid formulation could be retained at a core more effectively.

It was also found that the evaporation carrier with a density of 0.2 g/cm³ (in a range 0.15 to 0.25 g/cm³) could provide a larger liquid-absorption quantity by increasing the area of the evaporation carrier, thereby retaining the liquid formulation from the core more effectively.

For example, a liquid diffusing sheet can be configured so as to cover a surface which comes into contact with the liquid absorbing member of the evaporation carrier on the surface. Such a constitution allows the liquid formulation to diffuse over the evaporation carrier by the liquid diffusing sheet, and also allows the liquid formulation to spread to a larger area in a shorter time, thereby improving the perfume-rendering speed.

In this embodiment, the evaporation carrier may be available in a configuration other than a square, for example, a rectangle, oval form, circular form, polygon form, petal form, star or forms depicting animals or plants or any other forms.

In the evaporation apparatus of this embodiment, when the liquid formulation L contained in the retention vessel 31 is supplied to the body 35a of the evaporation carrier 35, said liquid formulation L is at first impregnated into over all the body 35a and then into the erected part 35b. Subsequently, volatile ingredients such as aromatic ingredients are evaporated from the upper surface of the body 35a as well as the surface, side face and back face of plural erected parts 35b. Ambient air enters into the outer vessel 32 through the evaporation aperture 37 not closed by the erected part 35b, and at the same time the air containing active ingredients in the outer vessel 32 are diffused out.

The liquid formulation L is quantitatively supplied to the evaporation carrier 35 through the liquid absorbing member 33 from the retention vessel 31.

According to the above-configured evaporation apparatus 30, active ingredients contained in the liquid formulation L can be evaporated sufficiently by erecting the erected part 35b from the body 35a of the evaporation carrier 35, due to an increased evaporation area of the evaporation carrier 35.

In addition, since the liquid formulation L contained in the retention vessel 31 is supplied through the liquid absorbing member 33 to the evaporation carrier 35, the liquid formulation L can be supplied quantitatively to the evaporation carrier 35, by which active ingredients contained in the liquid formulation L can be evaporated stably from the evaporation carrier 35.

In this embodiment, the liquid absorbing member 33 acts as a liquid absorbing mechanism and the evaporation carrier 35 acts as an evaporation mechanism. Further, the erected part 35b acts as a means for adjusting the evaporation of active ingredients.

In the evaporation apparatus 30 of this embodiment, screw threads may be provided as an engagement part at the site where the retention vessel 31 engages with the outer vessel 32. Screw threads may be used as an engagement part 28b so that the retention vessel 31 can be adjusted for the position in relation to the outer vessel 32 by rotating the retention vessel 31 upon application. Therefore, the supply quantity of the liquid formulation L can be adjusted by adjusting the distance between the liquid absorbing member 33 and the evaporation carrier 35. In place of screw threads, a shoulder may be used so that the retention vessel 31 can be adjusted for the position in relation to the outer vessel 32 by lowering or elevating the retention vessel 31 upon application.

Next, an explanation will be made for a modified example of the evaporation carrier of this embodiment.

Figure 11:
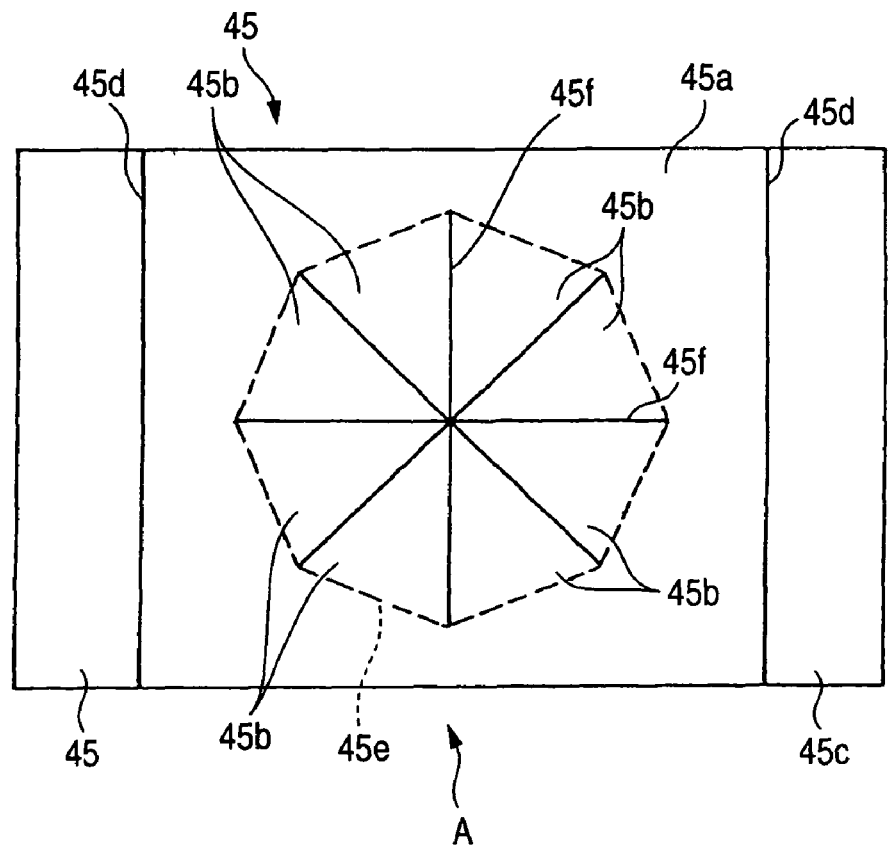
FIG. 11 is a top view showing a modified example of the evaporation carrier in FIG. 8.

FIG. 11 is a plain view showing a modified example of an evaporation carrier 45. FIG. 11 shows a body 45a in the state before erected parts 45b and 45c are erected. The evaporation carrier 45 is provided with grooves 45d and 45d extending inward along both the shorter sides of the rectangular evaporation carrier 45. An area enclosed between the grooves 45d and 45d is given as the body 45a, and an area out of the grooves 45d and 45d is given as the erected part 45c. Further, a groove 45e is provided on the back at the center of the body 45a in a form of a flat polygon (octagonal form in this instance). In addition, a dotted line 45f is formed toward the center from individual apexes of polygonal grooves 45e. The inner part of the groove 45e is divided into plural erected parts 45b (8 parts in this instance) by the dotted line 45f.

Figure 12:
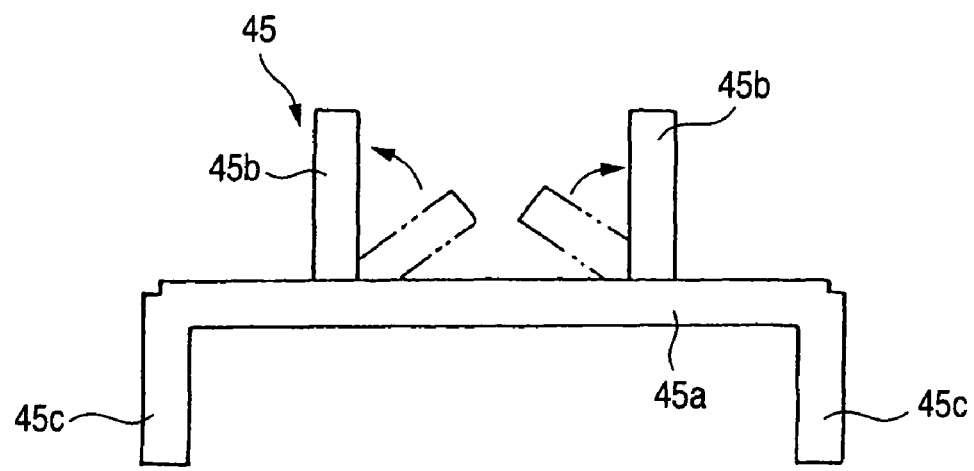
FIG. 12 is a side view of the evaporation carrier shown in FIG. 11.

In FIG. 11, the erected part 45c is erected toward the back in relation to the page surface and at the same time the erected part 45b is erected toward the front in relation to the page surface, by which, as shown in FIG. 12, the evaporation carrier 45 of this embodiment has the erected part 45b erected upward from the body 45a and the erected part 45c erected backward from the body. The erected part 45b is erected to provide an opening for ventilation at the center of the body 45a of the evaporation carrier 45, by which air flow inside the outer vessel housing the evaporation carrier 45 can be improved to obtain a better evaporation.

In this example, the erected part 45b is erected radially, with the center placed on a certain point at the body 45a (the center in this instance) like a so-called gate fold (double door), however, that is not restricted. The erected part may be erected from the body like a single swing door, for example. In these instances, the liquid absorbing member may be provided at such a site where the liquid formulation can be supplied to the evaporation carrier. Volatile ingredients can be evaporated sufficiently according to this embodiment.

EXAMPLE 1

An evaporation carrier was provided that was in a configuration as shown in FIG. 8, namely, the longer side L was 71 mm, the thickness was 6 mm and the groove 15d was 3 mm in width. The evaporation carrier with a density of 0.2 g/cm$^3$ was prepared with tissue for the front and the back surface and was made with pulp for the interior. The thus prepared evaporation carrier was housed in the outer vessel 32 in a state as shown in FIG. 6. The evaporation aperture 37 of the outer vessel 32 was made to be 30 cm$^2$ in total area. The liquid formulation with the following prescription (400 ml) was retained in a plastic retention vessel 31 having a 6.5 mm-diameter and 35 mm-long liquid absorbing member 33 made with the polyacrylic core (PA60) and the resin-made plug 34.

| (Ingredients) | (Quantity) |
|---|---|
| Alcohol (ethanol) | 5% by weight |
| Surfactant(polyoxyethylenealkylether) | 2.5% by weight |
| Lemon perfume | 2% by weight |
| Blue No. 1 | 0.0006% by weight |
| Yellow No. 4 | 0.002% by weight |
| Purified water | remaining quantity |

At 20° C. the liquid formulation was supplied from the retention vessel 31 to the above evaporation carrier to effect evaporation and observe a total evaporation quantity overtime. The total evaporation quantity was determined by measuring a gross weight of the evaporation apparatus.

For comparison, an evaporation carrier (comparison example 1) in a square form, and 71 mm in the side length L and 6 mm in thickness, without erected parts and subjected to similar tests was performed. Such an evaporation carrier was housed in a predetermined outer vessel and subjected to similar tests.

Figure 13:
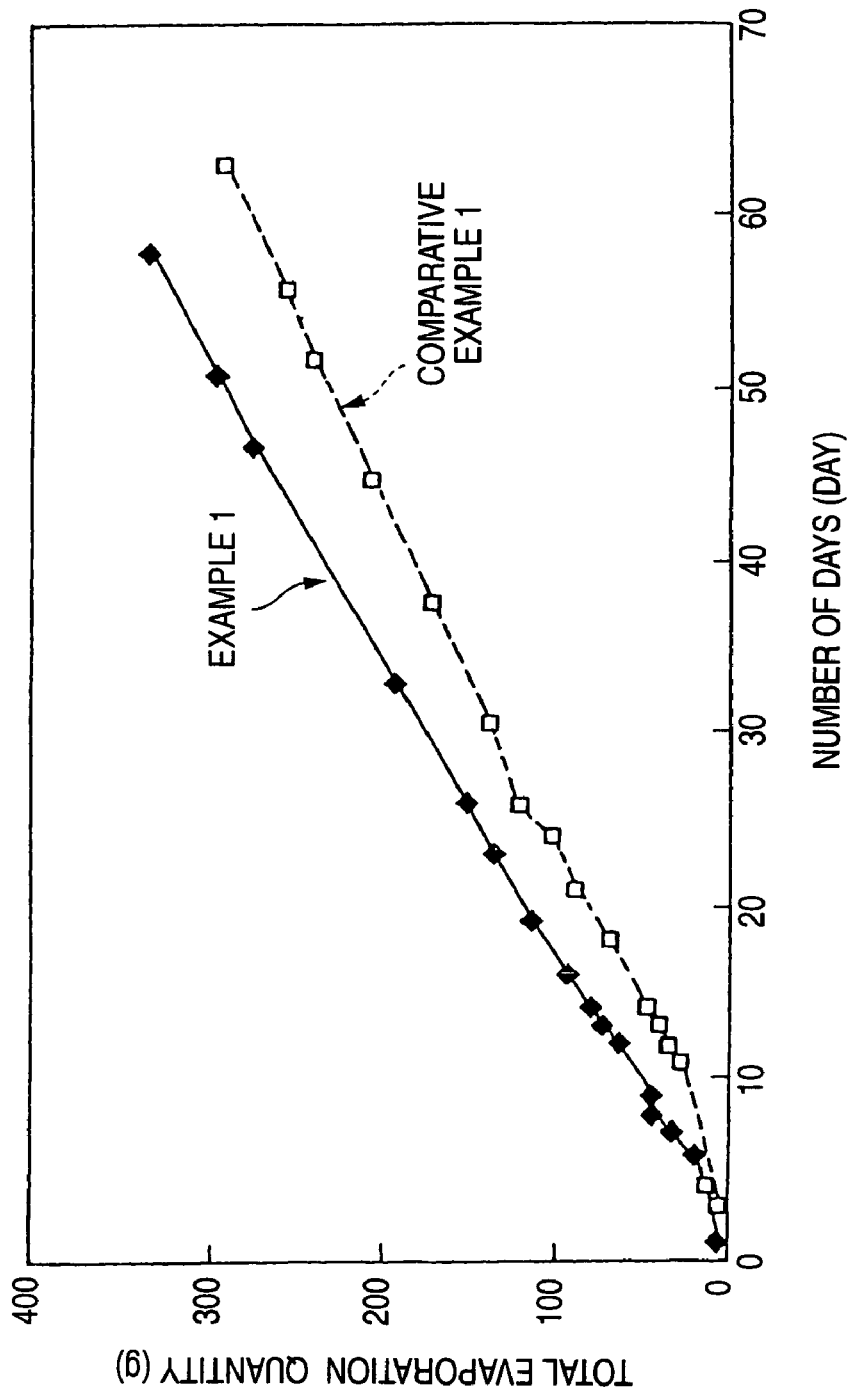
FIG. 13 is a graph showing the results of comparison tests.

The results are shown in FIG. 13. In Example 1, the total evaporation quantity reached 300 g in 50 days, but in the comparative example 1 the quantity did not reach 250 g in 50 days.

EXAMPLE 2

The evaporation carrier (78 mm in the side length L and 6 mm in thickness) having the 3 mm-wide thread 15d which was different in size from that described in Example 1 was provided and subjected to similar tests.

For comparison, an evaporation carrier (comparison example 2) in a square form, and 78 mm in the side length L and 6 mm in thickness, without erected parts and subjected to similar tests was performed.

Figure 14:
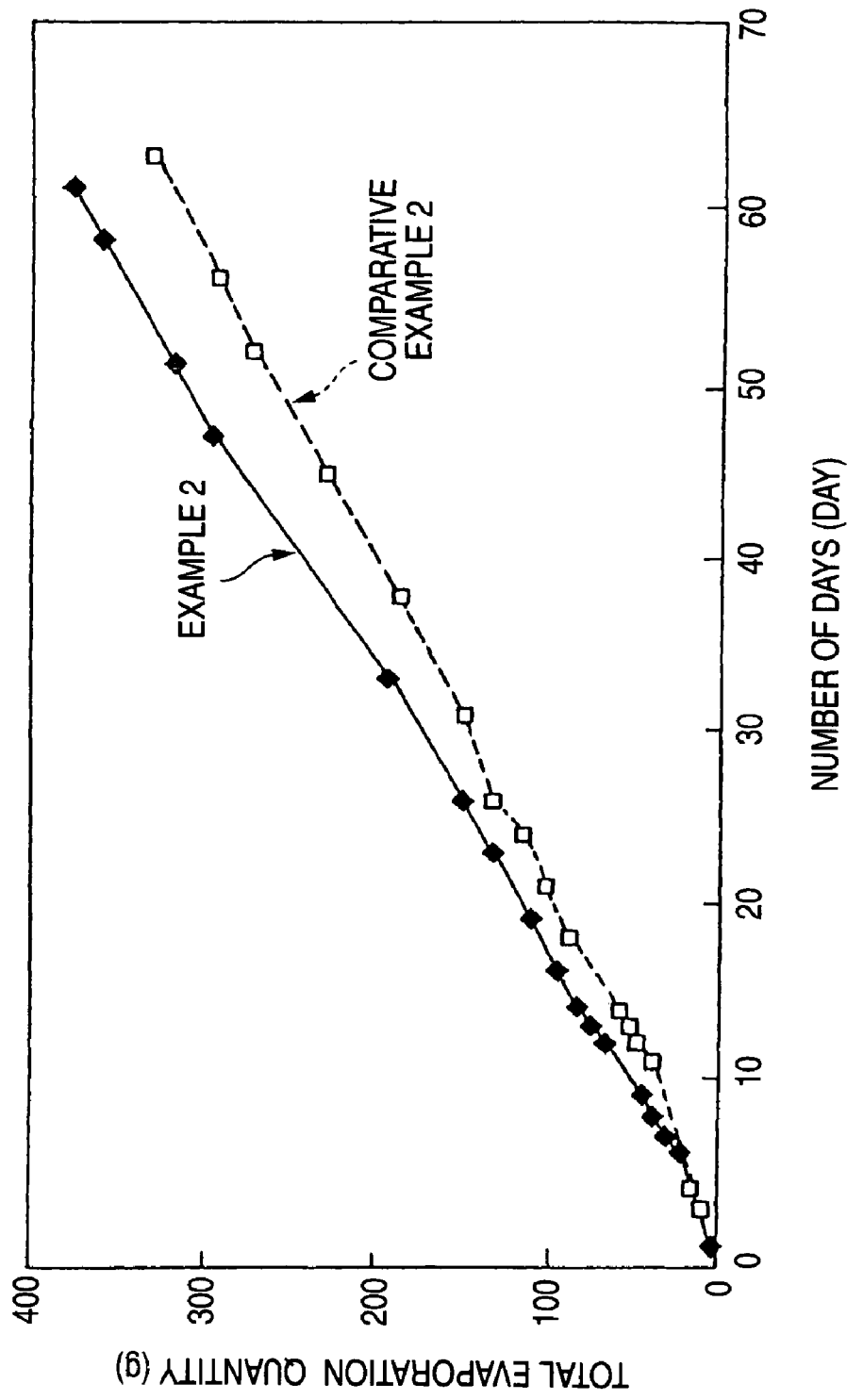
FIG. 14 is a graph showing the results of other comparison tests.

The results are shown in FIG. 14. In Example 2, the total evaporation quantity exceeded 320 g in 50 days, but in the comparative example 2 the quantity was about 280 g in 50 days. The aromatic effect obtained in Example 2 was superior to that obtained in Example 1 because the evaporation carrier was larger in the surface area than that in Example 1.

The following prescription may be used as a liquid formulation in this embodiment.

| (Ingredients) | (Quantity) |
|---|---|
| 95% ethanol | 5.0 g |
| Polyoxyethylenealkylether (solubilizing agent) | 3.0 g |
| Sodium ioctyl sulfosuccinate (solubilizing agent) | 7.0 g |
| Perfume (perfume-rendering agent) | 8.0 g |
| Vegetable extracted essence (deodorant) | 0.1 g |
| Isothiazoline antibacterial agent (antiseptic agent) | 0.1 g |
| Ultraviolet ray absorbing agent | 0.005 g |
| Silicone emulsion (antifoaming agent) | 0.0001 g |
| Pigment (coloring agent) | adequate quantity |
| Purified water (solvent) | adequate quantity |
| (Total) | 100 g |

Third Embodiment

Figure 15:
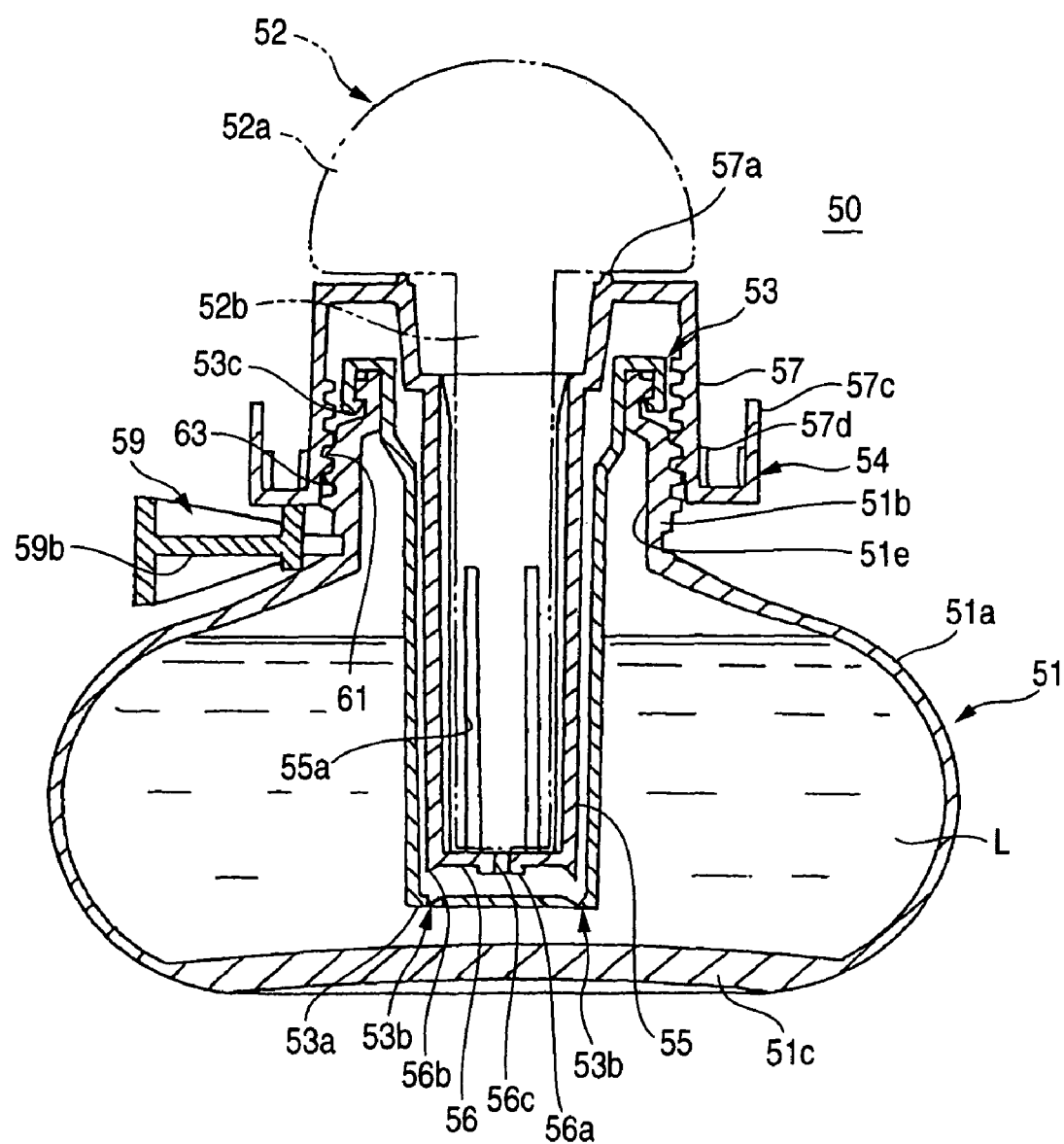
FIG. 15 is an overall cross-sectional view of the third embodiment of the evaporation apparatus in the invention.

As shown in FIG. 15, an evaporation apparatus 50 comprises an retention vessel 51 made with a resin (for example, PET) housing the liquid formulation L therein, a resin-made liquid absorbing member 52 to which the liquid formulation L is supplied, a shield member 53 provided so that the liquid absorbing member 52 will not contact with the liquid formulation L before use of the evaporation apparatus 50 (before use) and a lid member 54 fixed so as to be fitted with the retention vessel 51 for sealing the openings.

The retention vessel 51 is configured so as to have a body 51a in which a space is provided to house the liquid formulation L therein and a cylindrically standing part 52b erected upward from the body 51a (upward in relation to FIG. 15). An area enclosed by the standing part 51b of the body 51a is formed so that it can be opened, and an opening 51e is laid out by the inner circumferential surface of the standing part 51b. The standing part 51b is also provided with a male screw 63 on the outer circumferential surface. A bottom 51c of the retention vessel 51 may be provided with a slant part moving from the center toward the peripheral border of the bottom 51c and a groove slanting from the peripheral border toward the center. Such a constitution makes it possible to collect the liquid formulation L remaining around the center of the bottom 51c even when only a small quantity of the liquid formulation L remains therein and to use it until the very last.

The shield member 53 is tubular and inserted into the retention vessel 51 via the opening 51e. In this instance, the shield member 53 is positioned, with the one end immersed into the liquid formulation L in the retention vessel 51, and the end is sealed with an end face 53a. In other words, the shield member 53 is a tube with a bottom.

This shield member 53 is provided with a thinned part 53b notched along the outer circumference on the inside of the end face 53a which constitutes the bottom.

A jaw 53c is projected in a circular manner on the upper end of the shield member 53. The jaw 53c is engaged with the upper end of the standing part 51b of the retention vessel 51 for fixing, in a state where the shield member 53 is inserted into the retention vessel 51. In this instance, the shield member 53 is placed in such a way that the sealed lower edge is immersed into the liquid formulation L contained in the retention vessel 51, with a slight clearance provided from the bottom 51c of the retention vessel 51.

The shield member 53 may be made with resins, metals, water-resistant laminated materials, rubbers, wood and bamboo, for example.

The liquid absorbing member 52 has an evaporating part 52a exposed above a lid member 54 and a liquid absorbing part 52b for absorbing the liquid formulation L.

The lid member 54 has a column 55 extending into the retention vessel 51, and the liquid absorbing part 52b of the liquid absorbing member 52 is positioned inside of the column 55.

The column 55 is provided with plural slits 55a extending vertically at the front edge.

Figure 16:
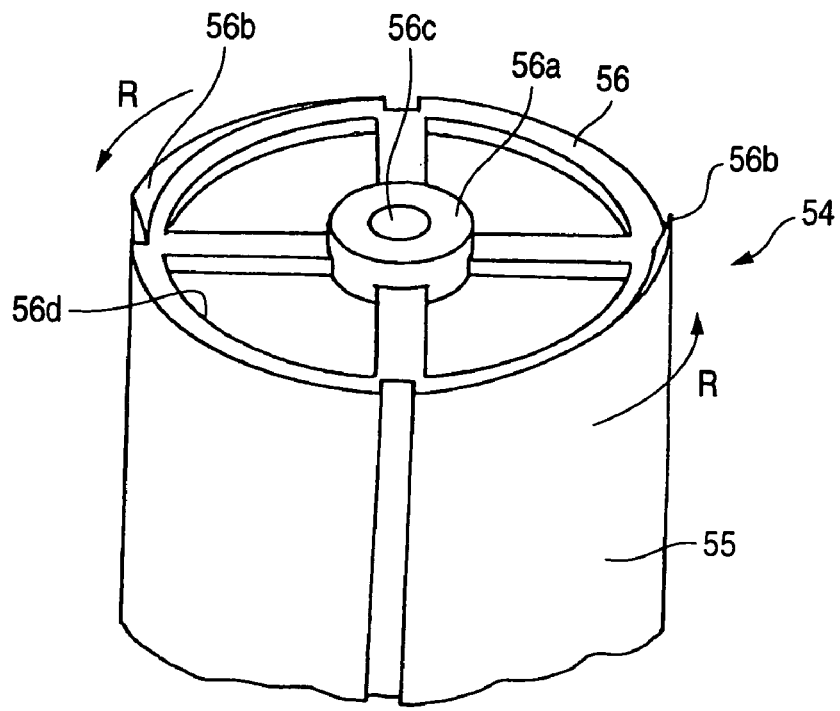
FIG. 16 is an enlarged view of the front edge of the column shown in FIG. 15.

FIG. 16 is a main part perspective view of the apical surface of the column shown in FIG. 15.

As shown in FIG. 16, the apical surface 56 of the column 55 has a projection 56a in which the aperture 56c communicating inside the column 55 is formed. Further, the apical surface 56 of the column 55 is provided with a pair of denticles 56b along the outer circumference. These denticles 56b are slightly further projected than the projection 56a formed at the center of the column 55. Further, the apical surface 56 of the column 55 is provided with plural openings 56d on the outer circumference of the projection 56a.

The lid member 54 has a head 57 folded back at the upper end of the column 55.

The head 57 is provided with a female screw 61 on the inner circumference and structured to mate with a male screw 63 provided on the standing part 51b of the retention vessel 51.

Figure 17:
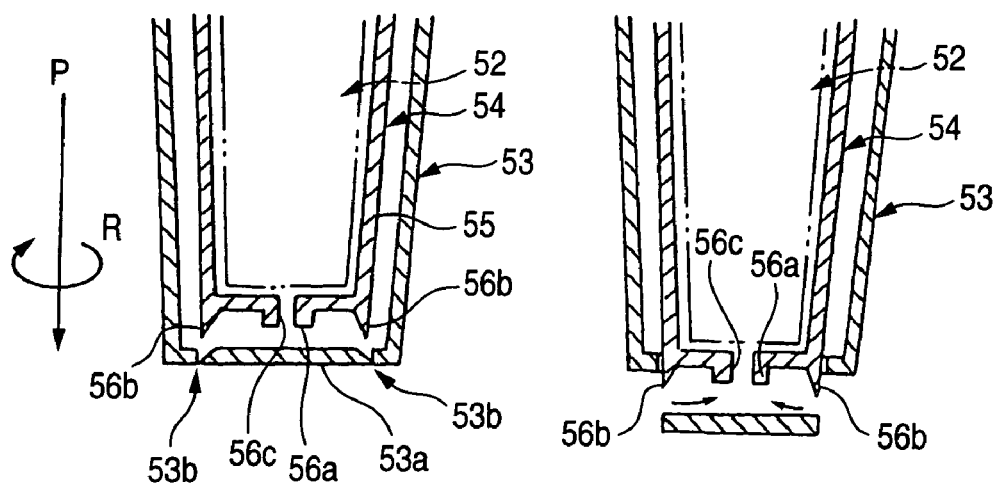
FIG. 17(a) is a cross-sectional view showing the positional relationship of the column and the shield member before use and the operating state.
FIG. 17(b) is a cross-sectional view showing a state where the shield member is broken with the edge of the column upon use.

As shown in FIG. 17(a), when the lid member 54 is turned toward the direction of R shown with the arrow in FIG. 17(a), with the head 57 held, the head 57 is screwed therein, by which the column 55 is pushed downward (toward P shown at the center of FIG. 17(a)), and the denticle 56b formed on the apical surface. 56 moves forward while sliding with the thinned part 53b on the end face 53a of the shield member 53, by which the end face 53a of the shield member 53 is broken and cut away, as shown in FIG. 17(b).

As shown in FIG. 16, the denticle 56b is formed so as to curve along the rotating direction R for screwing the lid member 54, and also slanted so as to gradually increase the degree of projection toward the rotating direction R in the lid member 54.

More particularly, in the denticle 56b having such a configuration, the denticle 56b can easily break the end face 53a of the shield member 53, by turning the lid member 54 to lower the column 55, cutting a desired area and moving apart for allowing the liquid supply.

As shown in FIG. 15 and FIG. 16, in the evaporation apparatus 50 of this embodiment, the projection 56a and the denticle 56b are positioned, with the clearance kept for keeping the liquid formulation L by surface tension. More particularly, a space between the projection 56a and the denticle 56b in the direction of the column diameter is provided so as to keep the liquid formulation L by surface tension.

Further, a clearance is provided between the projection 56a and the bottom 51c in a state where the denticle 56b is allowed to contact with the bottom 51c of the retention vessel 51. In other words, the evaporation apparatus is structured in such a way that the denticle 56b is allowed to contact with the bottom 51c of the retention vessel 51 while the projection 56a is not allowed to contact with the bottom 51c, in a state where the lid member 54 lowered as much as possible.

Figure 18:
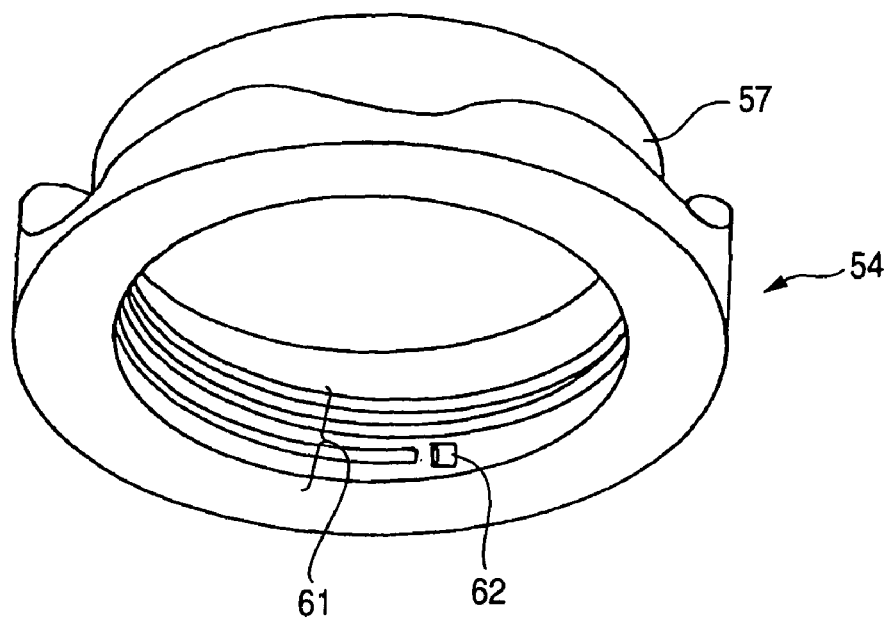
FIG. 18 is an enlarged perspective view of the lid member.

As shown in FIG. 18, the lid member 54 has the engagement projection 62 (first engagement projection) on the inner circumference having the female screw 61. In FIG. 18, the column is omitted and not illustrated for providing a better view.

Figure 19:
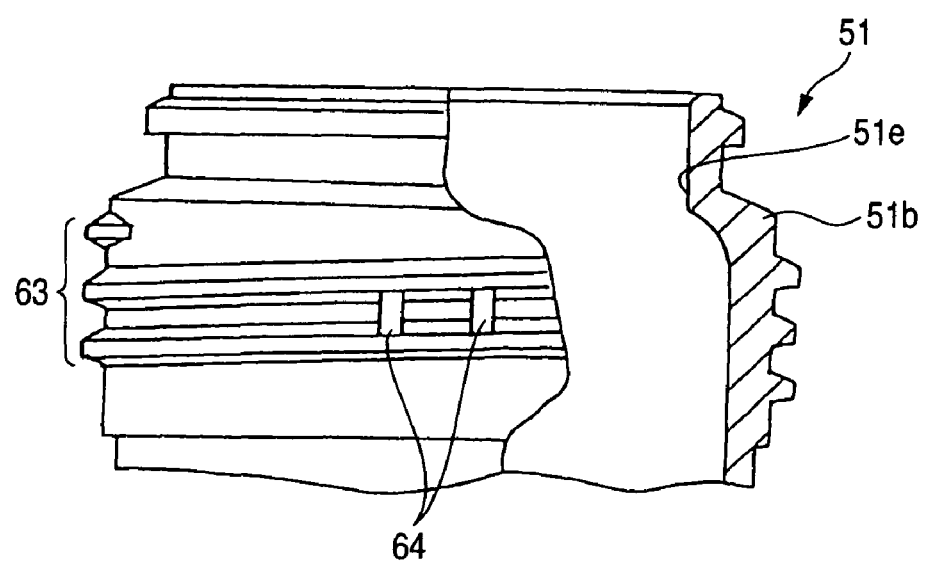
FIG. 19 is an enlarged view including the partial cross-sectional view of the opening on the retention vessel.
Figure 21:
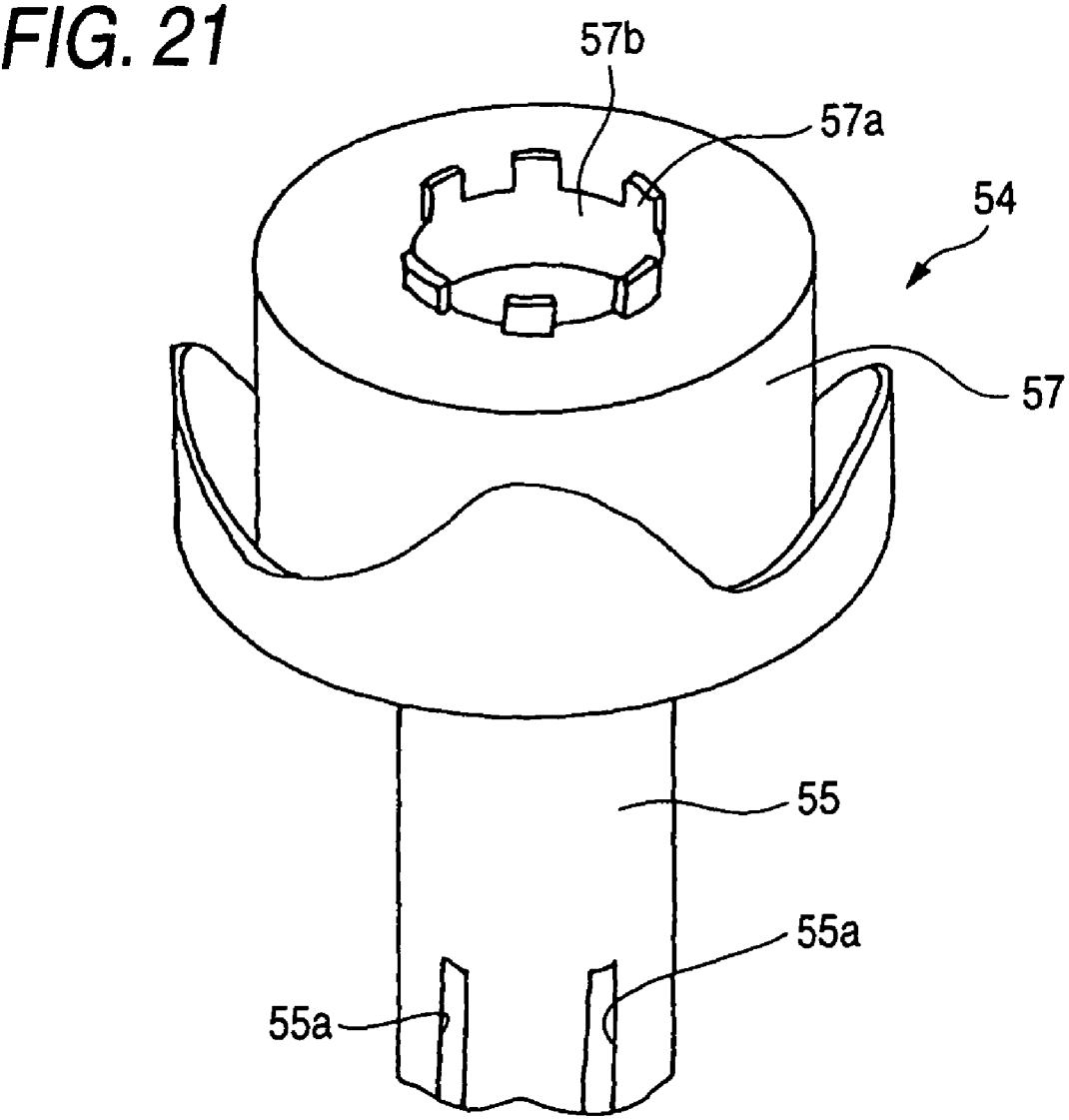
FIG. 21 is an overall perspective view of the lid member.

Further, as shown in FIG. 19, the standing part 51b of the retention vessel 51 is provided with a pair of engagement projections 64 (second engagement projection) on the outer circumferential surface having the male screw 63.

When the lid member 54 is fitted with the standing part 51b and turned downward, the engagement projection 62 on the lid member 54 is allowed to contact with one engagement projection 64 on the standing part 51b. An additional push and turn can provide the engagement projection 62 of the lid member 54 between other engagement projections 64 over the other adjacent engagement projection 64, thereby regulating the turn of the lid member 54.

As shown in FIG. 15, the standing part 51b of the retention vessel 51 is provided at the root with the stopper 59 which can attach to or detach from said standing part 51b.

As shown in FIG. 20, said stopper 59 is provided with a circular part 59a having a notched part 59c and a knob 59b formed on the side approximately opposite the notched part 59c.

The notched part 59c is placed on the root (refer to FIG. 15) of the standing part 51b of the retention vessel 51 and pushed forward to load the stopper 59, with the standing part 51b fitted with the circular part 59a. The lid member 54 is prevented from being lowered, in a state that the stopper 59 is applied to the standing part 51b.

The stopper 59 can be removed from the standing part 51b by pulling it, with the knob 59b grasped. The prevented depression of the lid member 54 is released by removing the stopper 59 from the standing part 51b.

As shown in FIG. 15 and FIG. 19, the lid member 54 is provided with plural supporting pieces 57a apart from each other in the circumferential direction on the border of the upper opening 57b at the upper end. Supporting pieces 57a support the liquid absorbing member 52 upward so that evaporating part 52a will not contact with the upper end face of the head 57 of the lid member 54, in a state that the liquid absorbing member 52 is applied into the evaporation apparatus 50. Therefore, air is appropriately supplied into the liquid absorbing part 52b from a space between the evaporating part 52a and the head 57, by which the liquid formulation L can be smoothly evaporated at the evaporating part 52a.

Next, an explanation will be made about the action of the above-structured evaporation apparatus 50, when it is used.

When the evaporation apparatus 50 is used, the stopper 59 attached to the root of the standing part 51b of the retention vessel 51 is pulled and removed, with the knob 59b grasped.

Next, the head 57 of the lid member 54 is grasped and turned toward the screwing direction (to the direction R as shown at the center of FIG. 17(a)).

Such action allows the engagement projection 62 on the lid member 54 provided between the engagement, projections 64 on the standing part 51b to ride over the engagement projection 64 in front of the screwing direction, thus releasing the restricted turn of the lid member 54.

Further, a turn of the lid member 54 allows the column 55 of the lid member 54 to turn and lower. The denticle 56b on the apical surface 56 of the column 55 moves forward, while sliding on the thinned part 53b on the end face 53a of the shield member 53, and further, the turn breaks and cuts away a part of the end face 53a of the shield member 53. The edge of the shield member 53 is opened and the denticle 56b contacts with the bottom 51c of the retention vessel 51, so that the projection 56a is positioned slightly apart from the bottom 51c of the retention vessel 51. In this instance, the denticle 56b may be configured so as to come close to the bottom 51c of the retention vessel (placed through a slight clearance), as long as inflow of the liquid formulation is not interrupted.

Such a configuration allows the liquid formulation L retained in the body 51a of the retention vessel 51 to flow into the column 55 from the end face 53a of the shield member 53 and flow therein also from the aperture 56c of the column 55, the opening 56d and the slit 55a. Said liquid formulation L is absorbed by the liquid absorbing part 52b of the liquid absorbing member 52.

The liquid formulation L absorbed by the liquid absorbing part 52b of the liquid absorbing member 52 is further absorbed by the liquid absorbing part 52b and evaporated into air from the evaporating part 52a on the upper end.

In this instance, the evaporating part 52a is positioned by the supporting piece 51a so as not to contact with the upper end of the lid member 54, with a clearance provided. Therefore, a space between the supporting pieces 57a is opened, from which open air is appropriately supplied into the retention vessel 51, thereby attaining a smooth absorption of the liquid formulation L into the liquid absorbing part 52b of the liquid absorbing member 52.

As explained above, in the evaporation apparatus of this embodiment, the projection 56a is positioned, with a slight clearance provided in relation to the bottom 51c of the retention vessel 51, in a state where the column member 55 is lowered upon use. Further, the projection 56a and the denticle 56b are positioned, via a clearance provided so as to retain the liquid formulation L by surface tension. Therefore, the liquid formulation L is evaporated more effectively and the liquid formulation L remains at a reduced quantity in the retention vessel 51. Further, even when the liquid formulation L remains only in a small quantity at the retention vessel 51, the liquid formulation L retained at the apical surface 56 is absorbed without fail via the aperture 56c by the liquid absorbing part 52b of the liquid absorbing member 52, by which the evaporation apparatus 50 is able to smoothly and completely absorb the liquid formulation L contained in the retention vessel 51.

Further, the above-structured evaporation apparatus 50 is free of the necessity for doing such troublesome work that users must remove the shield member 53 from the retention vessel 51 and again attach the lid member 54 to the retention vessel 51 so that the liquid absorbing member 52 can contact with the liquid formulation L upon use, which improves the usability and removes the problem where liquid formulation L adheres to the hands of users during the work.

The lid member 54 is not needed for being removed from the retention vessel 51, which can prevent the liquid formulation L from being leaked from the evaporation apparatus 50.

Since the shield member 53 can be broken by rotating the lid member 54 upon use, users do not need to apply a great force as compared with a case where the shield member 53 is just broken vertically.

In addition, there is no need to provide a so-called disposable cap which is taken out of the evaporation apparatus and disposed before use, which makes it possible to reduce the number of parts to be used in the evaporation apparatus. Furthermore, the evaporation apparatus 50 can be easily assumed for the usage during distribution and packed in a smaller container.

In the evaporation apparatus 50, engaging the engagement projection 62 of the lid member 54 together with the engagement projection 64 of the standing part 51b makes it possible to keep the lid member 54 fitted with the retention vessel 51, for example, in a case where the stopper 59 is not attached during the manufacturing process, thereby preventing the lid member 54 from an accidental turn before use.

In the above example, one engagement projection 62 is provided on the lid member 54, and two engagement projections 64 are provided on the standing part 51b. There are no restrictions on the number or the position of the engagement projections 62 and 64 in addition to the above example and, for example, two engagement projections 62 may be provided on the lid member 54 or one engagement projection 64 may be provided on the standing part 51b, as long as they can engage to prevent an accidental turn of the lid member 54.

Further, turning and lowering the lid member 54 makes it possible that the denticle 56b breaks the bottom 53a of the shield member 53, cutting apart a desired part of the end face 53a of the shield member 53, and dividing the shield member so that the liquid formulation L can flow into the column 55, thus, allowing the liquid formulation L contained in the retention vessel 51 to flow smoothly.

Users are able to grasp and pull out the knob 59b of the stopper 59 to remove the stopper 59 upon use, by which the inhibited turn of the lid member 54 is released to make the apparatus usable.

Further, when the shield member 53 is broken upon use, the liquid formulation L of the retention vessel 51 is supplied into the column 55 not only from the aperture 56c of the projection 56a but also from the slit 55a, by which the liquid formulation L can be more effectively absorbed by the liquid absorbing part 52b of the liquid absorbing member 52.

In this embodiment, the evaporation apparatus is configured in such a way that the evaporating part 52a acts as an evaporation mechanism and the liquid absorbing part 52b acts as a liquid absorbing mechanism. Further, a mechanism in which the end face 53a of the shield member 53 is broken by the denticle 56b provided on the apical surface 56 of the column 55, the liquid formulation L is supplied into the column 55 from the broken part and absorbed by the liquid absorbing part 52b acts as a means for adjusting the evaporation of active ingredients.

Fourth Embodiment

The evaporation apparatus of this embodiment is in principle similar in structure to that described in the third embodiment. This structure also provides similar effect as did previously. Therefore, the members, etc., similar in structure and action to those described in the third embodiment are given the same or corresponding symbols and thus explanation is simplified or omitted.

Figure 22:
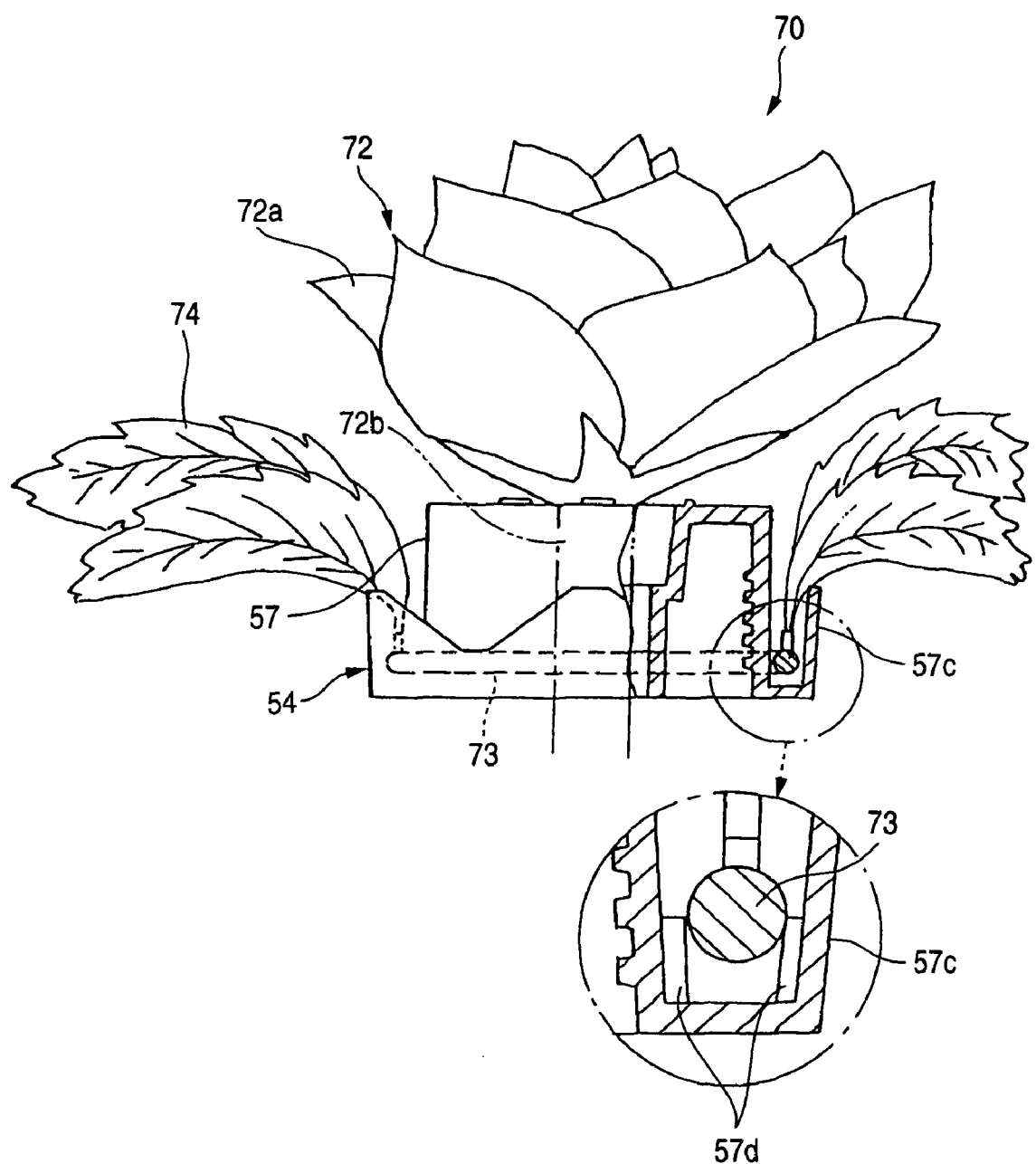
FIG. 22 is a main part enlarged view of the fourth embodiment of the evaporation apparatus in this invention.

As shown in FIG. 22, in an evaporation apparatus 70 of this embodiment a evaporating part 72a of a liquid absorbing member 72 is of a petal shape.

Further, a ring part 73 having a leaf modeled decoration 74 apart in the circumferential direction is set between the head 57 of the lid member 54 and the lower stop 57c. In this structure, users are able to turn the lid member 54 without touching the evaporating part 72a by grasping the lower stop 57c.

As explained above, the evaporation apparatus 70 of this embodiment has a flower-modeled configuration.

A pair of fitting pieces 57d is provided on the outer circumference of the head 57 and the inner circumference of the lower stop 57c. The ring part 73 set between the head 57 and the lower stop 57c is kept between the fitting pieces 57d, by which the decoration 74 can be firmly fixed to the lid member 54. In addition, when viewed from outside of the evaporation apparatus (for example, from the right in FIG. 22), the ring part 73 is housed into a space between the head 57 and the lower stop 57c and kept concealed, thus improving the decorative features.

In this embodiment, the liquid formulation includes perfumes and pigments. The perfume used in this embodiment is a synthetic perfume (Floral) (2% by weight) (oil-based perfumes may be used). Further, the pigment used here is an aqueous pigment Red No. 102 (0.001% by weight). These perfumes and pigments are dissolved in deionized water (a solvent) and added to the liquid formulation, together with an active material (polyoxyethylene hardened castor oil) at 2.5% by weight.

The evaporation carrier of this embodiment is 91 g/m$^2$ in weight and 337 cm$^2$ in the total evaporation area.

In addition, the liquid absorbing member is made with polypropylene/polyethylene compound fiber and 13 mm in the core diameter, 10 cm in length and 77% in porosity.

The evaporation apparatus of this embodiment is configured in such a way that the evaporation carrier acts as an evaporation mechanism and the liquid absorbing member acts as a liquid absorbing mechanism. Further, the evaporation apparatus of this embodiment is made similar in weight and the total evaporation area of the evaporation carrier as well as the material, core diameter, length and porosity of the liquid absorbing member to the case mentioned above, by which active ingredients can be adjusted for the evaporation. In other words, a combined mechanism of the liquid absorbing member and the evaporation carrier acts as a means for adjusting the active ingredients.

By referring to FIG. 15 and FIG. 22, it will be understood that the apparatus is configured in such a way that a liquid absorbing part 72b is able to adjust a quantity of the liquid formulation L supplied to a evaporating part 72a and the evaporating part 72a can be recognized from the pattern at the site where perfume or colored part is given from the liquid formulation L supplied.

More particularly, the liquid formulation L contained in the retention vessel 51 is absorbed by the liquid absorbing part 72b and supplied into the evaporating part 72a via the liquid absorbing part 72b. At the evaporating part 72a, solvents and perfumes excluding non-volatile pigments contained in the thus supplied liquid formulation will vaporize. Then, a site where pigments remain at the evaporating part 72a (hereinafter referred to as colored part) will be colored. In other words, it is understood that perfume is emitted from the colored part. Therefore, the evaporating part 72a (or the evaporation carrier 72) may be used to confirm the status of evaporating ingredients (aromatic ingredients) at the evaporator 70.

In this embodiment, a colored site of the evaporating part 72a is deeply colored from the front edge and colored over all the evaporating part 72a after a certain time (90 minutes) from the start of using the evaporator. In other words, the configuration (pattern) of the evaporating part 72a flexibly changes in the area depending on a quantity of the supplied liquid formulation L and becomes larger over time.

The pattern given by coloration on the evaporating part 72a will be decided for the configuration and the variation in the configuration by the liquid absorbing property of the evaporating part 72a and the liquid absorbing part 72b as well as by the volatility of the solvent.

Where the solvent vaporizes before the absorbed liquid formulation L arrives at the front edge of the evaporating part 72a, the pigment contained in the liquid formulation L will not arrive at the front edge of the evaporating part 72a. In this instance, no deep coloration is given to the front edge of the evaporating part 72a.

In other words, where the solvent vaporizes too quickly and disappears earlier than the rate of absorption at the evaporating part 72a, the solvent will vaporize before arrival of the pigment at the front edge, thus resulting in coloration halfway at the evaporating part 72a.

In contrast, where the liquid is absorbed up to the front edge of the evaporating part 72a before it vaporizes, the pigment is supplied sufficiently to the front edge of the evaporating part 72a, thus giving a deep coloration to the front edge of the evaporating part 72a. Namely, the pigment is non-volatile and moves inside the evaporation carrier 72 together with the solvent until the solvent vaporizes. Thus, adjusting the absorption rate and the volatilization rate can be appropriately controlled to decide patterns given to the evaporating part 72a.

The solvent maybe selected on the basis of the volatility at vapor pressure or at the boiling point to control the volatilization rate.

The evaporating part and absorbing part of the evaporation carrier may be selected for their materials by immersing them into the liquid to determine in advance the absorption rate. Further, the liquid absorbing part may be adjusted for the absorbing rate by referring to the measurement such as the length and diameter, or materials, porosity and others.

According to the evaporation apparatus of this embodiment, as the supplied liquid evaporates, the remaining pigment causes the pattern of the evaporation carrier to change. Such change in the pattern may be used to confirm the status of the evaporating ingredients in the evaporation apparatus and users may visually enjoy the decoration of the evaporation apparatus.

In this embodiment, the pigment may be included in advance into the evaporating part. Alternatively, the pigment may be included into both the liquid formulation and the evaporation carrier.

The following is an example of the liquid formulation used in the evaporation apparatus of this embodiment.

| (Ingredients) | (Quantity) |
|---|---|
| 3-methyl-3methoxy-1-butanol(Solfit) (solvent) | 10.0 g |
| 95% ethanol (solvent) | 5.0 g |
| Polyoxyethylene hardened castor oil (solubilizing agent) | 0.5 g |
| Perfume (perfume rendering agent) | 2.0 g |
| Vegetable extracted essence (deodorant) | 0.1 g |
| Isothiozoline-based antibacterial agent (antiseptic agent) | 0.1 g |
| Ultraviolet ray absorbing agent | 0.005 g |
| Pigment (coloring agent) | adequate quantity |
| Purified water | adequate quantity |
| (Total) | 100 g |

Next, an explanation will be made for a modified example of this embodiment by referring to FIG. 23 and FIG. 24.

Figure 23:
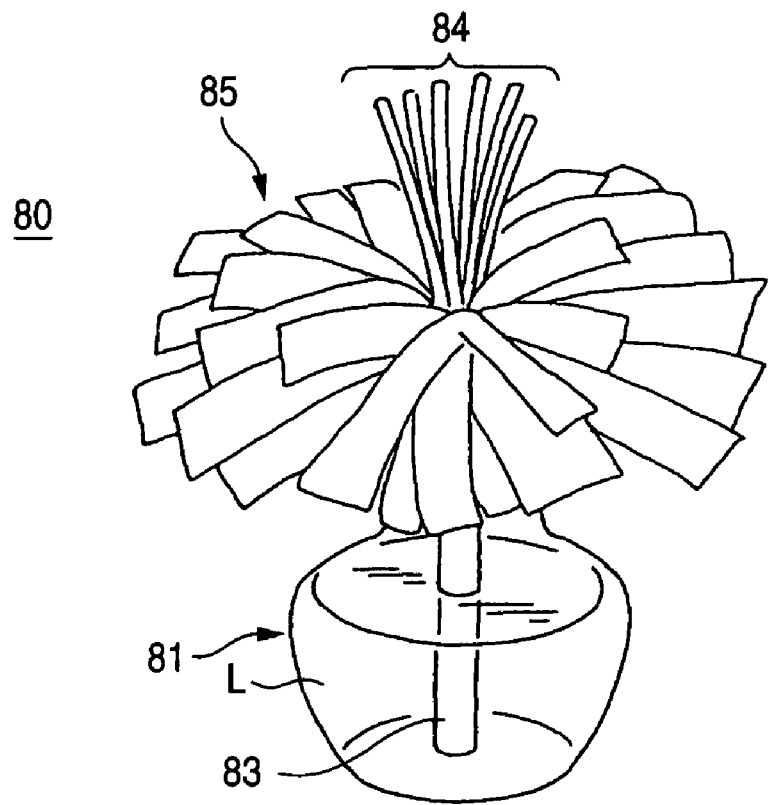
FIG. 23 is an overall perspective view showing a modified example of the evaporation apparatus shown in FIG. 22.

FIG. 23 is an overall perspective view showing a modified example of the evaporation apparatus of this embodiment. FIG. 24 is a cross-sectional view of the evaporation apparatus shown in FIG. 23. The members, etc., similar in structure and action to those described in the third embodiment are given the same or corresponding symbols and thus explanation is simplified or omitted.

An evaporator 80 shown in FIG. 23 comprises a retention vessel 81 housing the liquid formulation L which contains active ingredients therein, a liquid absorbing core (liquid absorbing member) 83 immersed into the liquid formulation L and an evaporating part 84 formed integrally with the liquid absorbing core 83. The number 85 shown in FIG. 23 is a petal part modeled after a petal.

Figure 24:
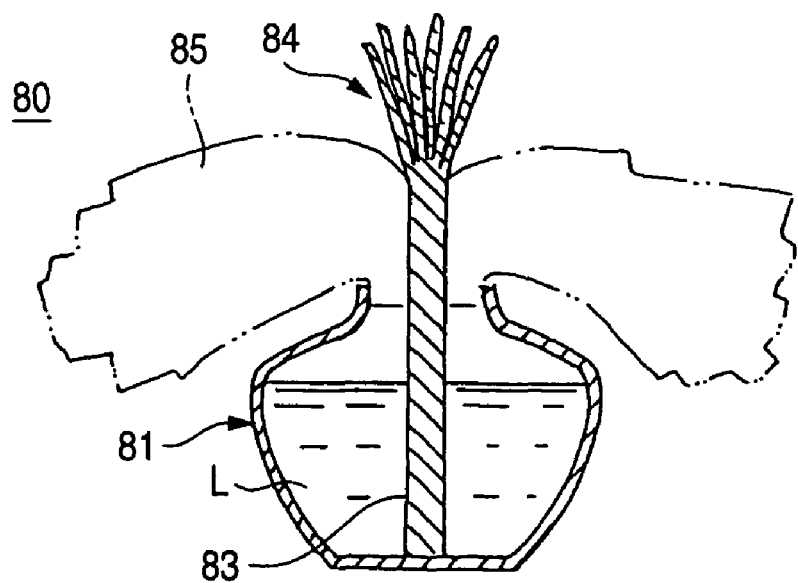
FIG. 24 is an overall cross-sectional view of the evaporation apparatus shown in FIG. 23.

As shown in FIG. 24, the retention vessel 81 is shaped into a hollow and approximately spherical form, into which the liquid formulation L is housed. An opening is provided at an upper part of the retention vessel 81, and the longitudinal liquid absorbing core 83 is passed through the opening. The liquid absorbing core 83 is positioned into the retention vessel 81 at one end and immersed into the liquid formulation L, while being lead out of the vessel through the opening at the other end. The end positioned out of the vessel of the liquid absorbing core 83 is branched into plural ends (6 ends in this embodiment) and a petal part 85 is provided on an outer circumferential surface close to the branching site. The branched site of the liquid absorbing core 83 is formed to model a stamen of a flower in a state of being assembled as the evaporation apparatus 80.

As the liquid formulation L and the liquid absorbing core 83, the items already explained may be used in this embodiment. In this embodiment, the liquid formulation is immersed in advance with perfumes or pigments as with the above embodiment. Further, the petal part 85 is made up with members which will not absorb the liquid formulation L.

In the evaporator 80, absorbing core 83 and evaporating part 84 are formed integrally. In other words, the liquid formulation L housed in the retention vessel 81 is absorbed upward from the liquid absorbing core 83 and arrives at the evaporating part 84 for evaporation.

In other words, the evaporator 80 is configured in such a way that it will not evaporate evaporating (aromatic) ingredients from the petal part 85 to which no liquid formulation L is supplied but will evaporate them only from the evaporating part 84 modeled after a stamen. Namely, the evaporating part 84 acts as an evaporation carrier. Although not illustrated here, the evaporator may be structured in such a way that an evaporating part modeled after a pistil or sepal is attached to a liquid absorbing member to evaporate evaporating ingredients from the evaporating part.

At the evaporating part 84 of the liquid absorbing core 83, the supplied liquid formulation L is evaporated to leave nonvolatile pigments, which deeply color the evaporating part 84.

According to the evaporation apparatus of this embodiment, the liquid is supplied to the evaporating part via the body of the liquid absorbing part, by which perfume or a colored part is given. Then, the evaporating part is colored by evaporating perfumes and allowing pigments to remain, and given a state as if a stamen of flower is colored. Thus, users are able to confirm the perfume status in the evaporator and also enjoy the decoration.

No restriction is given on the colored state of the evaporating part (evaporation carrier), namely, configuration of pattern, and any and all patterns maybe available in addition to the above described pattern. For example, three major patterns that can be conceived when a flower-type evaporation carrier is used are shown in FIGS. 25(*a*) to (*c*).

Figure 25A:
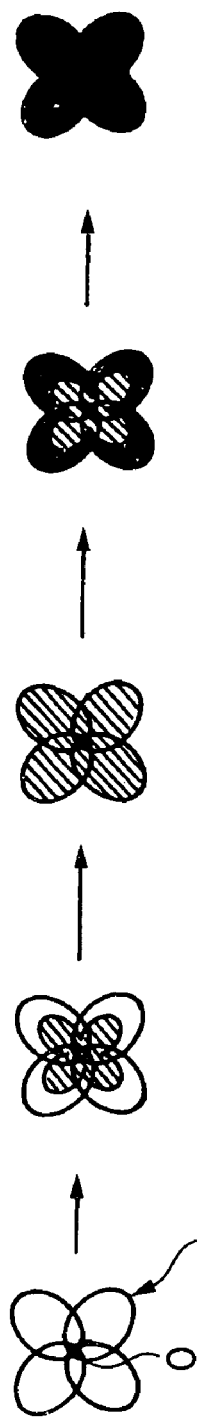
FIG. 25(a) is a diagram showing one example of coloring patterns of the evaporation carrier.
Figure 25B:
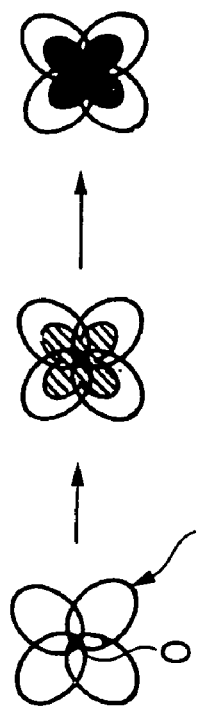
FIG. 25(b) is a diagram showing an example of coloring patterns of the evaporation carrier.
Figure 25C:
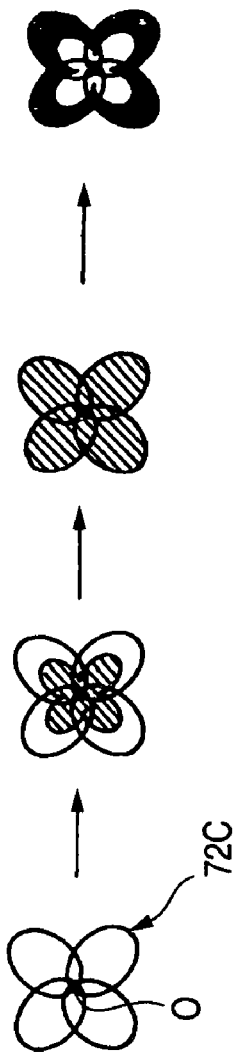
FIG. 25(c) is a diagram showing an example of coloring patterns of the evaporation carrier.

As shown in FIGS. 25(*a*) to (*c*), these three patterns consist of type A, type B and type C, which are different in the sites (patterns) colored with the lapse of time or respectively at 72A, 72B and 72C of flower-modeled evaporating parts (evaporation carrier). The evaporating parts, 72A, 72B and 72C, are all positioned vertically in relation to the drawing so that the liquid absorbing part (liquid absorbing member) which is not illustrated here can pass through the center O. Thus, they are structured to supply the liquid formulation from the liquid absorbing part.

As shown in FIG. 25(*a*), in the evaporating part 72A designated as type A, the liquid formulation is supplied to the evaporating part 72A from the liquid absorbing member sitting at the center O immediately after start of the supply, and an area in the vicinity of the center O is gradually colored, resulting in an overall coloration which is uniform and sparse. Then, with the lapse of time, color becomes darker along the border of the evaporating part 72A and finally (after passage of the previously determined time) develops into a state where the evaporating part is colored uniformly and deeply as a whole.

As shown in FIG. 25(*b*), in the evaporation body 72B designated as type B, the liquid formulation is supplied to the evaporating part 72B from the liquid absorbing member positioned at the center of O immediately after start of the supply, and as with the type A, an area in the vicinity of O is colored gradually. However, with the lapse of time, color in the vicinity of the center O becomes darker as it is, but the border is not colored finally and only the area in the vicinity of the center O is colored deeply.

As shown in FIG. 25(*c*), in the evaporating part 72C designated as type C, the liquid formulation is supplied to the evaporating part 72C from the liquid absorbing member positioned at the center O immediately after start of the supply, and an area in the vicinity of the center O is gradually colored, which is the same with type A and type B. However, with the lapse of time, the evaporating part 72C is colored uniformly and sparsely as a whole, and the color becomes deeper over time along the border of the evaporating part 72C. And, finally, the evaporating part 72C is not colored deeply as a whole, and only the border is deeply colored.

In a case where the evaporation carrier, the liquid absorbing member and the liquid formulation were attached to the evaporators shown in the Examples from 1 to 5 in the table below, these evaporators were actually used in test to evaluate a quantity of evaporation, colored state of the evaporation carrier, state of perfume and others.

TABLE 3

| | | Test results | | | | |
|---|---|---|---|---|---|---|
| | | Example 1 | Example 2 | Example 3 | Example 4 | Example 5 |
| Configuration of flower | | Large | Large | Bouquet (3 flowers) | Bouquet (3 flowers) | Margurette (3 flowers) |
| Evaporation carrier | Type | Filter paper | Filter paper | Crope paper | Japanese paper for calligraphy | Filter paper |

TABLE 3-continued

Test results

|  |  | Example 1 | Example 2 | Example 3 | Example 4 | Example 5 |
| --- | --- | --- | --- | --- | --- | --- |
|  | Weight | 91 g/m² | 91 g/m² | 49 g/m² | 24 g/m² | 91 g/m² |
|  | Total evaporation area | 337 cm² | 337 cm² | 540 cm² | 540 cm² | 111 cm² |
| Liquid absorbing member | Material | Polypropylene/ polyethylene composite fiber | Polypropylene/ polyethylene composite fiber | Polyester | Polyester | Polyester |
|  | Core diameter | φ13 mm | φ13 mm | φ2 mm | 2 mmφ | φ3 mm |
|  | Length | 10 cm | 10 cm | 10 cm | 10 cm | 10 cm |
|  | Porosity | 77% | 77% | 66% | 66% | 60% |
| Liquid formulation | Solvent | Deionized water | Isobar-H | Deionized water | Deionized water | Deionized water |
|  | Perfume concentration | 2% | 2% | 2% | 2% | 2% |
|  | Pigment concentration | Aqueous pigment Red No. 102 0.001% | Oil soluble pigment Red No. 225 0.001% | Aqueous pigment Red No. 102 0.001% | Aqueous pigment Red No. 102 0.001% | Aqueous pigment Red No. 102 Yellow No. 4 Blue No. 1 0.001% |
|  | Activating agent concentration (Marpon SG200) | 2.5% | 2.5% | 2.5% | 2.5% | 2.5% |
| Evaporation quantity (initial stage) |  | 24.0 g/day | 9.7 g/day | 24.4 g/day | 25.4 g/day | 17.6 g/day |
| Coloration method |  | Liquid is colored | Liquid is colored | Liquid is colored | Liquid is colored | Liquid is colored |
| Coloration state |  | Type A | Type A | Type B | Type A | Type C |
| Perfume state |  | Favorable | Favorable | Favorable | Favorable | Favorable |
| Retention of configuration |  | Retention | Retention | Retention | Retention | Retention |

As shown in table 1, the Examples 1 and 2 were similar in structure to the evaporation apparatus 70 given in FIG. 22. However, in the Example 1 deionized water was used as a solvent, whereas in the Example 2 Isobar-H was used as a solvent. In the Example 1, Red No. 102 was used as a pigment whereas in the Example 2, Red No. 225 (oil-based pigment) was used as a pigment. Other members not specified here (for example, retention vessel) were all the same as those used in the evaporation apparatus 70.

The coloration method used in the Examples from 1 through 4 was such that pigments were dissolved in the liquid formulation. The method used in the Example 5 was such that a pigment dissolved in an absorption member was previously poured. The perfume and the activating agent used in the liquid formulation were of the same concentration. Further, a synthetic perfume (Floral) was used in the Examples 1, 3 and 4, whereas an oil-based perfume was used in the Example 2.

In this test, those clearly showing a change in the color of the evaporation carrier were considered to be favorable in the coloration state.

Regarding the test results of the Examples 1 and 2, there was no problem on an initial quantity of evaporation (quantity of evaporation determined for one day from the start of use), namely, 24.0 g in the Example 1 and 9.7 g in the Example 2. The state of perfume was favorable and no deterioration was found in the configuration of the evaporation carrier modeled after a flower.

Figure 26:
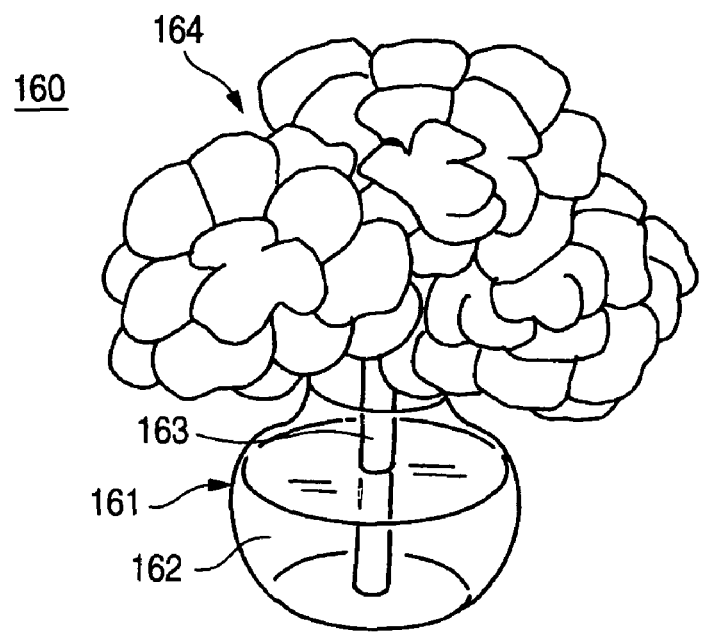
FIG. 26 is an overall perspective view showing one example of the evaporation apparatus of the embodiment.

As shown in FIG. 26, in the Example 3, an evaporation carrier 164 of an evaporation apparatus 160 had a bouquet-like flower configuration of three flowers bound together, and crepe paper was used as an evaporation carrier 164. In this instance, the bouquet-like flower represented a configuration of plural flowers bound together.

A liquid absorbing member 163 shown in the Example 3 was made with polyester, having the core diameter of 2 mm and length of 10 cm. The liquid absorbing member was 66% in porosity.

A liquid formulation 162 used in the Example 3 was the same as that used in the Example 1.

Regarding the test result of the Example 3, an initial quantity of the evaporation was 24.4 g/day. The state of coloration was of the type B pattern as shown in FIG. 25(*b*) and in a final state only the area in the vicinity of the liquid absorbing member was deeply colored. The state of perfume was favorable, and the configuration of the evaporation carrier was well kept and not deteriorated.

Similarly as in the Example 3, in the Example 4, the evaporation carrier had a configuration of bouquet-like flowers. Japanese paper for calligraphy was used as an evaporation carrier, which was 24 g/m² in weight and 540 cm² in the total evaporation area.

The liquid absorbing member and the liquid formulation used in the Example 4 were the same as those used in the Example 3.

Regarding the test results of the Example 4, an initial quantity of evaporation was 25.4 g/day and the coloration state of the evaporation carrier was of the type A as shown in FIG. 25(*a*). The state of perfume was favorable, and the configuration of the evaporation carrier was well kept and not deteriorated.

Figure 27:
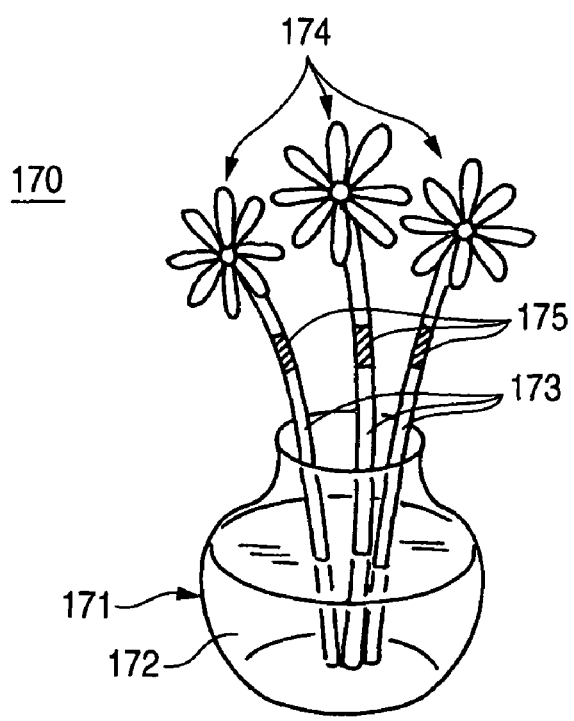
FIG. 27 is an overall perspective view showing one example of the evaporation apparatus described in another embodiment.

In the Example 5, an evaporation carrier 174 of an evaporation apparatus 170 had a configuration of a marguerite-like flower as shown in FIG. 27. In this instance, the marguerite-like flower represented a configuration in which similar-shaped evaporation carriers (petals) 174 were superimposed up and down. Filter paper was used as an evaporation carrier 174 in the Example 5, which was 91 g/m² in weight and 11 cm² in the total evaporation area.

A liquid absorbing member 173 used in the Example 5 was made with polyester, having the core diameter of 3 mm, length of 10 cm and porosity of 60%.

In the Example 5, deionized water was used as a solvent and Red No. 102, Yellow No. 4 and Blue No. 1 were used as pigments (concentration of 0.001%) to prepare a liquid formulation 172.

In the evaporation apparatus 170 of this Example, colored water with a high concentration (pigment) was in advance permeated into at an intermediate part 175 of a liquid absorbing core (liquid absorbing member) 173. Then, the colorless liquid formulation 172 absorbed from the liquid absorbing core 173 was mixed with the colored water stored at the intermediate part 175 to give a colored solution, which moved to the evaporation carrier 174 over time. The evaporation carrier 174 had a configuration of flower modeled after circular petals and changed as if an actual flower is colored through supply of the colored liquid formulation 172.

Regarding the test results of the Example 5, an initial quantity of evaporation was 17.6 g/day, and the coloration of the evaporation carrier 174 was of the type C as shown in FIG. 25(*c*). The state of perfume was favorable and the configuration of the evaporation body was well kept and not deteriorated.

In this instance, when plural evaporation carriers (3 in FIG. 27) having a flower-modeled configuration are provided with liquid absorbing cores individually impregnated with differently colored water and immersed into a similar liquid formulation, evaporation bodies are colored differently. In other words, the evaporators are provided with an appearance with different flowers coming out.

The above test has revealed that when the evaporation carrier, the liquid absorbing member and the solution are appropriately controlled, the evaporator can be kept favorable in the state of perfume and at the same time coloration of the evaporation body can be changed.

Figure 28A:
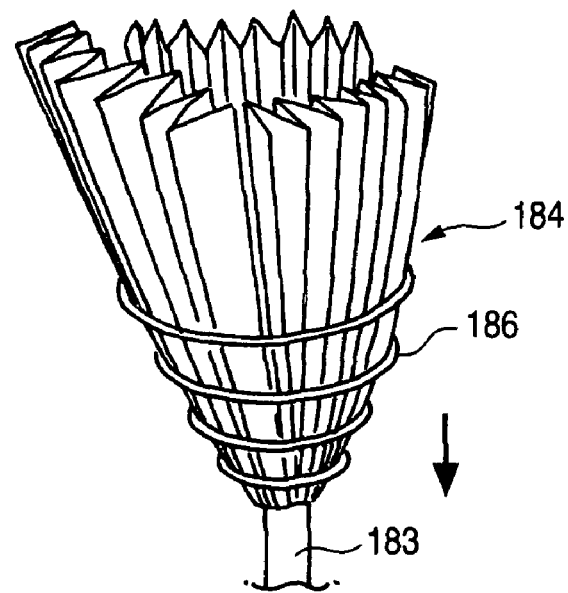
FIG. 28(a) is a main part perspective view of a modified example of the evaporation apparatus described in FIG. 22, showing a state where the evaporation carrier is folded down.
Figure 28B:
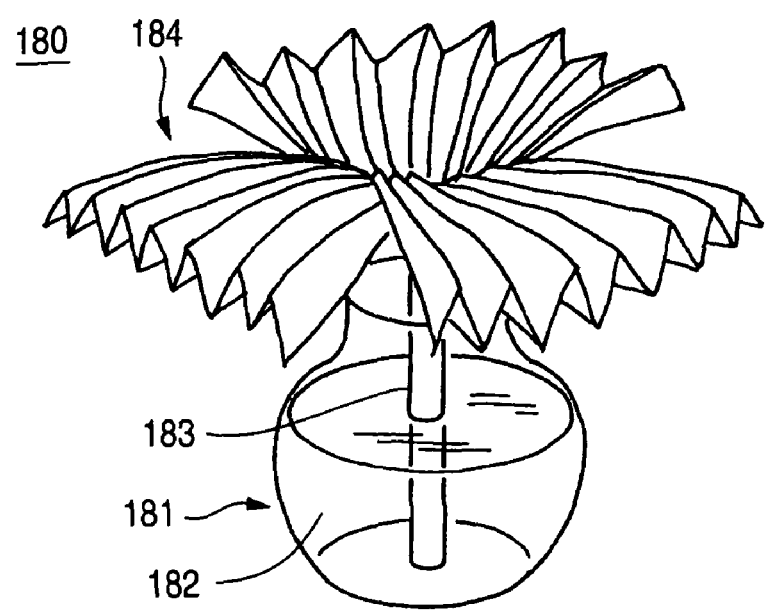
FIG. 28(b) is an overall perspective view showing the evaporation carrier of the evaporation apparatus given in FIG. 28(a) in an extended state.

Further, in this embodiment, for example, a flower-modeled evaporation body may be structured so as to be opened or closed by means of an elastic body such as a wire or spring. An example of the evaporation apparatus with such a structure is shown in FIG. 28(*a*) and 28(*b*). As shown in FIG. 28(*a*), an evaporation apparatus 180 is structured so as to prevent an evaporation carrier 184 from being opened by providing plural evaporation carriers 184 (3 in this FIG.) which are folded several times and bound together and fitting an elastic body (spiral spring) 186 around the thus fabricated evaporation carriers. Since the evaporation apparatus is structured as such, it can be packed in a smaller container, with the evaporation carrier folded down.

The evaporation apparatus 180 is also structured so as to expand the folded evaporation carrier 184 upon use as shown in FIG. 28(*b*) by removing the elastic body 186 in the direction of the arrow as shown in FIG. 28(*a*) (or in the direction opposite the arrow).

In this embodiment, an aperture may be provided for supplying externally the liquid formulation to the retention vessel of the evaporation apparatus, by which the liquid formulation can be poured whenever necessary or added appropriately when it is used up.

As in the above embodiment, the evaporation apparatus may have the shield member covering the outer circumference of the liquid absorbing member, by which the liquid absorbing member is not immersed with the liquid before use to prevent evaporating ingredients from volatilization into air.

The retention vessel may have a vase-like configuration, for example. Therefore, where a flower-modeled evaporation carrier is attached to the vessel, the evaporation apparatus is given an appearance as if real flowers have been placed, thus improving the decorative features.

The present invention has been explained in detail and by referring to specific embodiments, and it should be quite clear for those skilled in the art that various changes and modifications can be made without departing from the spirit and scope of this invention.

INDUSTRIAL APPLICABILITY

Since the evaporation apparatus according to this invention is able to adjust the evaporation of active ingredients by adjusting means, active ingredients contained in the liquid formulation can be prevented from evaporation before use. Adjusting active ingredients so as to evaporate in a necessary and sufficient quantity upon use makes it possible to keep the effect of active ingredients for a long period.

What is claimed is:

1. A non-heating evaporation apparatus comprising a retention vessel keeping a liquid formulation which contains active ingredients, a liquid absorbing mechanism which absorbs the liquid formulation from said retention vessel, and an evaporation mechanism which evaporates the active ingredients of said liquid formulation absorbed into said liquid absorbing mechanism, wherein the liquid formulation is prepared by adding water into at least one of glycols, lower alcohols and 3-methyl-3-methoxy-1-butanol so as to have a chemical concentration of 0.2 to 20% by weight, the liquid absorbing mechanism comprises a liquid absorbing core that is a felt core, biscuit core, pulp core, inorganic substance-forming core, or resin liquid absorbing member, the liquid absorbing mechanism further comprises an evaporation carrier to which the liquid formulation is supplied via said liquid absorbing core, a liquid absorbing velocity of the liquid absorbing core from one end to the other end is 1 to 40 hours, the evaporation carrier is provided with a body having a density of 0.15 to 0.25 g/cm³ or a body having a liquid absorption quantity exceeding 15 g after 60 minutes when the carrier has an area of 60 cm², a lower part of a liquid absorbing member is exposed downward from said retention vessel, and means for adjusting the evaporation of the active ingredients, said means comprising the liquid absorbing core and the evaporation carrier.

2. The evaporation apparatus of claim 1 further comprising said liquid absorbing member immersed in advance or upon use in the liquid formulation in which at least either of perfume or pigment is dissolved with a solvent and an evaporation carrier which is attached integrally or separately with said liquid absorbing member and which is at least partially exposed out of said retention vessel wherein said solvent is adjusted for feeding by said liquid absorbing member and said evaporation carrier to effect evaporation, by which patterns changing with the lapse of time are imparted to said evaporation carrier.

3. A non-heating evaporation apparatus comprising a retention vessel keeping a liquid formulation which contains active ingredients, a liquid absorbing mechanism which absorbs the liquid formulation from said retention vessel, and an evaporation mechanism which evaporates the active ingredients of said liquid formulation absorbed into said liquid absorbing mechanism, wherein the liquid formulation is prepared by adding water into at least one of glycols, lower alcohols and 3-methyl-3-methoxy-1-butanol so as to have a chemical concentration of 0.2 to 20% by weight, the liquid absorbing mechanism comprises a liquid absorbing core that is a felt core, biscuit core, pulp core, inorganic substance-forming core, or resin liquid absorbing member, the liquid absorbing mechanism further comprises an evaporation carrier to which the liquid formulation is supplied via said liquid absorbing core, a liquid absorbing velocity of the liquid absorbing core from one end to the other end is 1 to 40 hours, the evaporation carrier is provided with a body having a density of 0.15 to 0.25 g/cm$^3$ or a body having a liquid absorption quantity exceeding 15 g after 60 minutes when the carrier has an area of 60 cm$^2$ and a thickness of 5mm and a plurality of erection parts erected from the body made of the same material as the body between which a notch is formed, and a lower part of a liquid absorbing member is exposed downward from said retention vessel, and means for adjusting the evaporation of the active ingredients, said means comprising the liquid absorbing core and the evaporation carrier.

4. A non-heating evaporation apparatus comprising a retention vessel keeping a liquid formulation which contains active ingredients, a liquid absorbing mechanism which absorbs the liquid formulation from said retention vessel, and an evaporation mechanism which evaporates the active ingredients of said liquid formulation absorbed into said liquid absorbing mechanism, wherein the liquid formulation is prepared by adding water into at least one of glycols, lower alcohols and 3-methyl-3-methoxy-1-butanol so as to have a chemical concentration of 0.2 to 20% by weight, the liquid absorbing mechanism comprises a liquid absorbing core that is a felt core, biscuit core, pulp core, inorganic substance-forming core or resin liquid absorbing member, the liquid absorbing mechanism further comprises an evaporation carrier to which the liquid formulation is supplied via said liquid absorbing core, a liquid absorbing velocity of the liquid absorbing core from one end to the other end is 1 to 40 hours, the evaporation carrier is provided with a body having a density of 0.15 to 0.25 g/cm$^3$ or a body having a liquid absorption quantity exceeding 15 g after 60 minutes when the carrier has an area of 60 cm$^2$, a lower part of a liquid absorbing member is exposed downward from said retention vessel, the erection part includes a pair of first erection portions provided on the other side of the body, a second erection portion that is erected into an opposite direction to the first erection portions, and that is divided in a circumferential direction around the center of the body, and means for adjusting the evaporation of the active ingredients, said means comprising the liquid absorbing core and the evaporation carrier.

5. The evaporation apparatus of any one of claims 1, 3, and 4 wherein said liquid absorbing mechanism is said liquid absorbing member at least partially exposed out of said retention vessel, and wherein said evaporation apparatus further comprises a cylindrical inner member fixed so as to cover the exposed part of said liquid absorbing member, a cylindrical outer member fixed so as to cover said inner member and a rotating part attached to said inner member or said outer member, wherein an inner opening is provided on said inner member and an outer opening is provided on said outer member, and rotation of said rotating part allows said inner opening and said outer opening to communicate, by which said liquid absorbing member is exposed to evaporate the active ingredients.

6. The evaporation apparatus of any one of claims 1, 3, and 4 comprising said retention vessel having said liquid absorbing member at a lower part which is at least partially exposed out of said retention vessel and said evaporation carrier to which said liquid formulation is supplied through said liquid absorbing member, wherein said evaporation carrier is shaped into a plate shape and made with porous materials.

7. The evaporation apparatus of any one of claims 1, 3, and 4 comprising said retention vessel having said liquid absorbing member at a lower part which is at least partially exposed out of said retention vessel and said evaporation carrier to which said liquid formulation is supplied through said liquid absorbing member, wherein said liquid absorbing member contacts with said evaporation carrier on the surface.

8. The evaporation apparatus of any one of claims 1, 3, and 4 wherein said liquid absorbing mechanism is said liquid absorbing member immersed in advance or upon use in the liquid formulation in which at least either of perfume or pigment is dissolved with a solvent and wherein said evaporation apparatus further comprises an evaporation carrier which is attached integrally or separately with said liquid absorbing member and which is at least partially exposed out of said retention vessel, wherein said solvent is adjusted for feeding by said liquid absorbing member and said evaporation carrier to effect evaporation, by which patterns are imparted to said evaporation carrier.

9. A non-heating evaporation apparatus comprising a retention vessel keeping a liquid formulation which contains active ingredients, a liquid absorbing mechanism which absorbs the liquid formulation from said retention vessel, and an evaporation mechanism which evaporates active ingredients of said liquid formulation absorbed into said liquid absorbing mechanism, wherein the liquid formulation is prepared by adding water into at least one of glycols, lower alcohols and 3-methyl-3-methoxy-1-butanol so as to have a chemical concentration of 0.2 to 20% by weight;

the liquid absorbing mechanism comprises a liquid absorbing core that is a felt core, biscuit core, pulp core, inorganic substance-forming core, or resin liquid absorbing member, the liquid absorbing mechanism further comprises an evaporation carrier to which the liquid formulation is supplied via said liquid absorbing core, a liquid absorbing velocity of the liquid absorbing core from one end to the other end is 1 to 40 hours, the evaporation carrier is provided with a body having a density of 0.15 to 0.25 g/cm$^3$ or a body having a liquid absorption quantity exceeding 15 g after 60 minutes when the carrier has an area of 60 cm$^2$, a lower part of a liquid absorbing member is exposed downward from said retention vessel, and evaporation of the active ingredients are adjusted by the liquid absorbing core and the evaporation carrier further comprising the liquid absorbing member to which said liquid formulation is supplied, a shield member set in such a manner that said liquid absorbing member will not contact with said liquid formulation before use and a lid member capable of fitting with said retention vessel so as to seal an upper opening of the retention vessel before use, wherein said lid member is provided with a column extended into said retention vessel in which said liquid absorbing member is housed, an apical surface of said column is provided with a projection at which an aperture communicating inside said column is formed and a denticle which breaks a part of said shield member by lowering said lid member upon use, and there is a clearance between said central part and said bottom in such a state that said denticle is kept in contact with or close to the bottom of said retention vessel.

10. The evaporation apparatus of claim 9 wherein said projection and said denticle are placed with a clearance capable of keeping said liquid formulation by surface tension.

11. The evaporation apparatus of claim 9 wherein said lid member is provided with a first engagement projection and said retention vessel is also provided with a second engagement projection capable of retaining a position at which said lid member fits with said retention vessel by allowing the first engagement projection to engage therewith.

12. The evaporation apparatus of claim 9 wherein said denticle is provided so as to curve toward the direction of rotating said lid member on the above apical surface and also slanted so as to increase an extent of forward projection gradually toward the rotating direction of said lid member.

13. The evaporation apparatus of claim 9 wherein a stopper is fixed which can be removed upon use, while preventing said lid member from lowering before use, and the stopper is provided with a knob.

14. The evaporation apparatus of claim 9 wherein said column is provided with a slit extending vertically toward said column.

15. The evaporation apparatus of any of claims 9 to 14, wherein the liquid absorbing member is immersed in advance or upon use in the liquid formulation in which at least either of perfume or pigment is dissolved with a solvent and the evaporation carrier is attached integrally or separately with said liquid absorbing member and is at least partially exposed out of said retention vessel, and wherein said solvent is adjusted for feeding by said liquid absorbing member and said evaporation carrier to effect evaporation, by which patterns are imparted to said evaporation carrier.

16. The evaporation apparatus of any of claims 9 to 14, wherein the liquid absorbing member is immersed in advance or upon use in the liquid formulation in which at least either of perfume or pigment is dissolved with a solvent and the evaporation carrier is attached integrally or separately with said liquid absorbing member and is at least partially exposed out of said retention vessel, and wherein said solvent is adjusted for feeding by said liquid absorbing member and said evaporation carrier to effect evaporation, by which patterns changing with the lapse of time are imparted to said evaporation carrier.

17. A non-heating evaporation apparatus comprising a retention vessel keeping a liquid formulation which contains active ingredients, a liquid absorbing mechanism which absorbs the liquid formulation from said retention vessel, and an evaporation mechanism which evaporates active ingredients of said liquid formulation absorbed into said liquid absorbing mechanism, wherein the liquid formulation is prepared by adding water into a least one of glycols, lower alcohols and 3-methyl-3-methoxy-1-butanol so as to have a chemical concentration of 0.2 to 20% by weight, the liquid absorbing mechanism comprises a liquid absorbing core that is a felt core, biscuit core, pulp core, inorganic substance-forming core, or resin liquid absorbing member, an evaporation carrier to which the liquid formulation is supplied via said liquid absorbing core, a liquid absorbing velocity of the liquid absorbing core from one end to the other end is 1 to 40 hours, the evaporation carrier is provided with a body having a density of 0.15 to 0.25 g/cm$^3$ a body having a liquid absorption quantity exceeding 15 g after 60 minutes when the carrier has an area of 60 cm$^2$, an evaporation portion shaped as a flower made of a material that is 24 g/m$^2$ in weight, and means for adjusting the evaporation of the active ingredients, said means comprising the liquid absorbing core and the evaporation carrier.

* * * * *